(12) United States Patent
Matter et al.

(10) Patent No.: US 11,130,678 B2
(45) Date of Patent: Sep. 28, 2021

(54) CARBON FORMATION REACTOR AND METHOD OF USING SAME

(71) Applicant: pH Matter, LLC, Columbus, OH (US)

(72) Inventors: Paul H. Matter, Columbus, OH (US); Michael G. Beachy, Gahanna, OH (US); James Gaydos, Hilliard, OH (US)

(73) Assignee: Paul H. Matter, Columbus, OH (US)

( * ) Notice: Subject to any disclaimer, the term of this patent is extended or adjusted under 35 U.S.C. 154(b) by 182 days.

(21) Appl. No.: 15/654,996

(22) Filed: Jul. 20, 2017

(65) Prior Publication Data

US 2018/0023200 A1 Jan. 25, 2018

Related U.S. Application Data

(60) Provisional application No. 62/364,468, filed on Jul. 20, 2016.

(51) Int. Cl.
| | | |
|---|---|---|
| *C01B 32/164* | (2017.01) | |
| *B01D 53/86* | (2006.01) | |
| *B01D 53/96* | (2006.01) | |
| *C01B 32/15* | (2017.01) | |
| *C01B 32/16* | (2017.01) | |
| *C01B 32/162* | (2017.01) | |

(Continued)

(52) U.S. Cl.
CPC ............ *C01B 32/164* (2017.08); *B01D 53/46* (2013.01); *B01D 53/864* (2013.01); *B01D 53/96* (2013.01); *C01B 32/15* (2017.08); *C01B 32/16* (2017.08); *C01B 32/162* (2017.08); *F23K 5/002* (2013.01); *B01D 53/76* (2013.01); *B01D 53/81* (2013.01); *C02F 1/283* (2013.01); *C07C 1/12* (2013.01); *C12M 43/02* (2013.01); *C12M 43/06* (2013.01); *C25B 1/04* (2013.01); *Y02E 60/36* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 2006/0057054 A1* | 3/2006 | Fujioka | B82Y 30/00 423/447.2 |
| 2006/0099136 A1* | 5/2006 | Dillon | D01F 9/127 423/447.3 |

(Continued)

FOREIGN PATENT DOCUMENTS

| | | | | |
|---|---|---|---|---|
| WO | WO-2013158159 A1 * | 10/2013 | | B01J 19/02 |
| WO | WO-2013158161 A1 * | 10/2013 | | B01J 23/745 |

(Continued)

OTHER PUBLICATIONS

Holmes et al., Bosch CO2 Reduction System Development, Final Report; General Dynamics Convair Division; Apr. 1976. 38 pgs.

(Continued)

*Primary Examiner* — Clare M Perrin

(57) ABSTRACT

A novel carbon formation reactor for forming carbon from a carbon-bearing fluidic stream, and method of using the same, is described. The reactor uses a catalyst bearing surface placed within a heated zone in a carbon-bearing fluidic stream to form carbon, which can then be removed from the reactor, with the process repeatable to achieve high extraction efficiencies.

24 Claims, 22 Drawing Sheets

(51) Int. Cl.
*F23K 5/00* (2006.01)
*B01D 53/46* (2006.01)
*B01D 53/76* (2006.01)
*B01D 53/81* (2006.01)
*C25B 1/04* (2021.01)
*C07C 1/12* (2006.01)
*C12M 1/00* (2006.01)
*C02F 1/28* (2006.01)

(56) References Cited

U.S. PATENT DOCUMENTS

2010/0240529 A1* 9/2010 Balzano ............... B01J 23/88
  502/159
2012/0195821 A1* 8/2012 Sun ................... C01B 32/174
  423/448
2015/0064092 A1* 3/2015 Noyes ................. B01J 23/745
  423/304

FOREIGN PATENT DOCUMENTS

WO   WO-2014150944 A1 * 9/2014 ............... C01B 3/38
WO   WO-2014151144 A1 * 9/2014 .......... B01J 23/8892

OTHER PUBLICATIONS

Abney et al., Series-Bosch Technology For Oxygen Recovery During Lunar or Martian Surface Missions, 44th International Conference on Environmental Systems, Jul. 13-17, 2014, Tucson, Arizona, 14pgs.

* cited by examiner

Schematic of the 2.5-cm OD reactor test configuration.

Table 1. Initial Substrate Tests

| Test Number | Support | Catalyst | Gas Flow (sccm) | T (°C) | C Rate (g/gcat/hr) | C Rate (mg/cm²/hr) | Carbon Yield (%) |
|---|---|---|---|---|---|---|---|
| 18-26 | Direct on cloth | Fe/Co nitrate | 55 | 475 | 0.39 | 6.60 | 3.8 |
| 18-28 | Direct on cloth | Fe/Co nitrate | 10 | 475 | 0.15 | 2.24 | 7.1 |
| 18-31 | Nano-fiber coated cloth | Fe/Co nitrate | 55 | 475 | 1.28 | 9.27 | 5.3 |
| 18-33 | Nano-fiber coated cloth | Fe/Co nitrate | 10 | 475 | 0.64 | 5.00 | 15.8 |
| 18-42 | Nano-fiber coated cloth | Fe/Co metal (red.) | 10 | 475 | 0.14 | 1.14 | 3.6 |
| 18-48 | Nano-fiber coated cloth | Fe nitrate | 10 | 475 | 0.35 | 2.03 | 7.3 |
| 18-47 | Nano-fiber coated cloth (cleaned) | Fe/Co nitrate | 10 | 475 | 0.52 | 3.75 | 11.9 |
| 18-51 | Nano-fiber coated cloth (cleaned) | Fe/Co nitrate | 10 | 500 | 0.46 | 3.68 | 11.6 |
| 18-50 | Nano-fiber coated cloth (cleaned) | Fe/Co nitrate | 10 | 525 | 0.57 | 3.85 | 12.1 |
| 18-49 | Nano-fiber coated cloth (cleaned) | Fe/Co nitrate | 10 | 550 | 0.45 | 3.40 | 10.7 |
| 18-54 | Nano-fiber coated cloth (cleaned) | Fe/Co nitrate | 10 | 475 | 0.42 | 4.48 | 14.1 |
| 18-56 | Nano-fiber coated cloth (cleaned) | Fe nitrate | 10 | 475 | 0.34 | 2.58 | 8.1 |
| 18-61 | Nano-fiber coated cloth (cleaned) | Fe/Co nitrate | 3 | 475 | 0.23 | 1.89 | 19.8 |
| 18-60 | Nano-fiber coated cloth (cleaned) | Fe nitrate | 10 | 475 | 0.28 | 2.30 | 7.3 |
| 18-62 | Direct on cloth, in situ reduction | Fe/Co nitrate | 10 | 475 | 0.32 | 5.41 | 17.1 |
| 18-65 | Direct on cloth, external reduction | Fe/Co nitrate | 10 | 475 | 1.00 | 4.94 | 15.6 |
| 18-63 | Direct on cloth, external reduction | Fe nitrate | 10 | 475 | 0.34 | 2.24 | 7.1 |
| 18-68 | Direct on cloth, in situ reduction | Fe/Co nitrate | 3 | 475 | 0.17 | 2.86 | 30.3 |
| 18-71 | Direct on cloth, in situ reduction | Fe/Co nitrate | 10 | 450 | 0.83 | 4.60 | 14.5 |
| 18-72 | Direct on cloth, in situ reduction | Fe/Co nitrate | 10 | 425 | 0.80 | 5.03 | 15.9 |
| 18-73 | Direct on cloth, external reduction | Fe/Co nitrate | 10 | 475 | 0.35 | 6.59 | 20.8 |
| 18-80 | Direct on cloth, in situ reduction | Fe/Co nitrate | 10 | 475 | 0.78 | 5.52 | 15.6 |
| 18-82 | Direct on cloth, in situ reduction | Fe/Co nitrate | 10 | 475 | 0.73 | 5.03 | 14.2 |
| 18-84 | Direct on cloth, in situ reduction | Fe/Co nitrate | 10 | 475 | 0.64 | 3.89 | 10.9 |
| 18-86 | Direct on cloth, in situ reduction | Fe/Co nitrate | 50 | 300 | 0.33 | 1.89 | 1.1 |
| 18-89 | Direct on cloth, in situ reduction | Fe/Co nitrate | 50 | 350 | 0.53 | 3.65 | 2.1 |
| 18-90 | Direct on cloth, in situ reduction | Fe/Co nitrate | 50 | 375 | 0.81 | 4.65 | 2.6 |
| 18-95 | Direct on cloth, in situ reduction | Fe/Co nitrate | 50 | 400 | 0.76 | 4.37 | 2.5 |
| 18-103 | Direct on cloth, in situ reduction | Fe/Co nitrate | 10 | 475 | 0.83 | 5.06 | 14.3 |
| 18-104 | Lower Binder - Direct on Cloth | Fe/Co nitrate | 10 | 475 | 0.84 | 4.81 | 13.5 |
| 18-105 | Direct on cloth, in situ reduction | Fe/Co nitrate | 10 | 475 | 1.21 | 6.93 | 19.5 |
| 18-93 | Direct on cloth, in situ reduction | Fe/Co nitrate | 50 | 475 | 1.49 | 8.54 | 4.8 |
| 18-110 | Direct on cloth, in situ reduction | Fe/Co nitrate | 10 | 475 | 0.86 | 5.45 | 19.5 |
| 18-113 | Direct on cloth, in situ reduction | Fe/Co nitrate | 10 | 475 | 0.96 | 5.49 | 19.7 |

Fig. 2

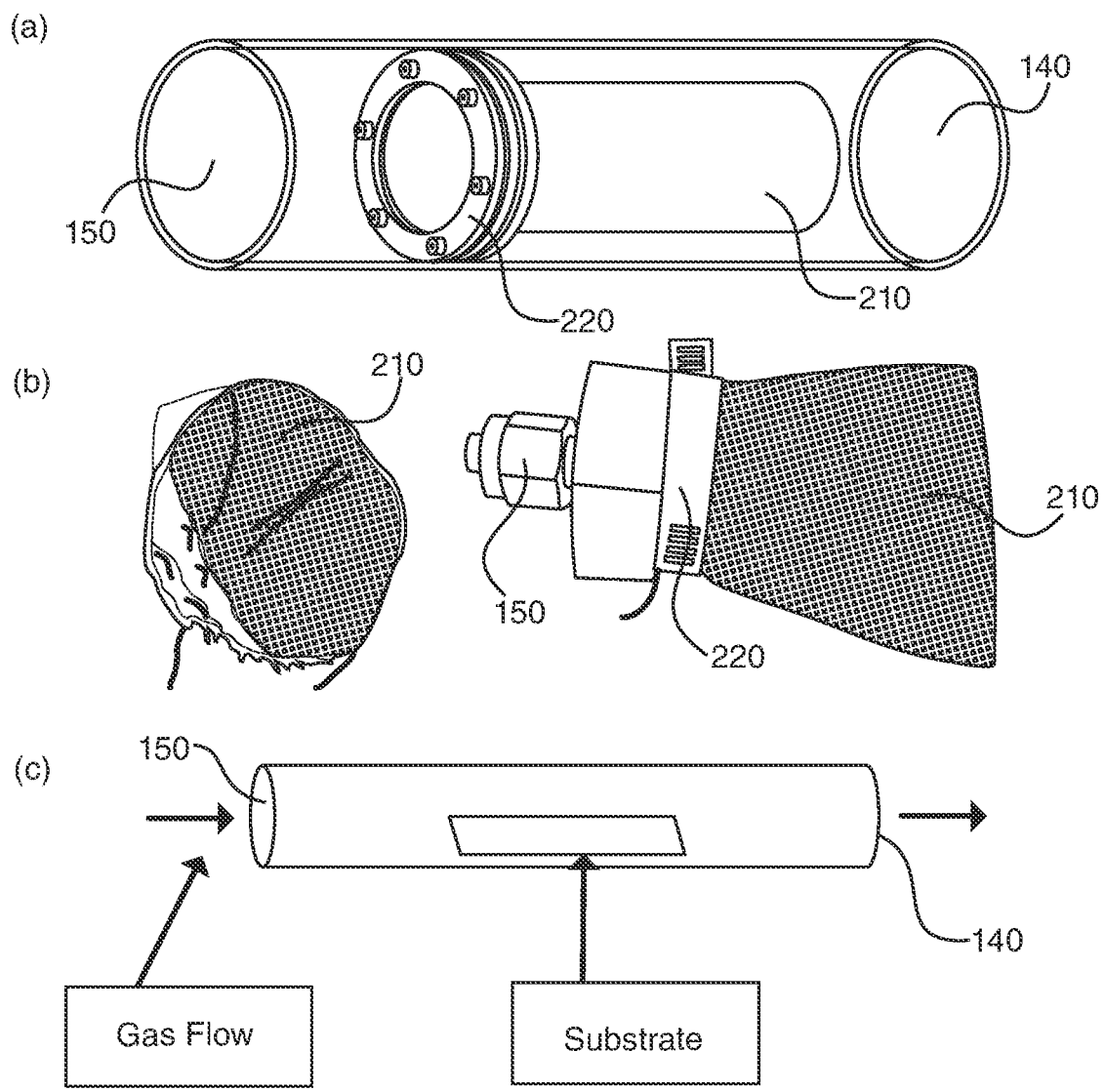
Examples of test configurations at the 7.5 -cm OD scale.
Fig. 3 (a-c)

Table 2. Overview of Single-Cycle Test Results in the 7.5 cm OD Test Stand

| Test Number | Sample Description | Time (hrs) | Gas Flow (sccm) | T (°C) | C Rate (g/gcat/hr) | C Rate (mg/cm$^2$/hr) | Carbon Yield (%) |
|---|---|---|---|---|---|---|---|
| 18-85 | Coarse weave tube, painted | 18 | 200 | 475 | 0.33 | 2.02 | 7.1 |
| 18-87 | Fine weave, painted | 66 | 200 | 475 | 0.43 | 2.62 | 8.8 |
| 18-97 | Fine weave, sprayed | 100 | 200 | 475 | 0.35 | 2.06 | 8.3 |
| 18-106 | Fine weave, sprayed | 18 | 200 | 475 | 0.37 | 2.52 | 10.1 |
| 18-108 | Fine weave, sprayed heavier | 66 | 200 | 475 | 0.23 | 2.24 | 9.0 |
| 18-111 | Fine weave, sprayed, wide opening | 48 | 200 | 475 | 0.36 | 2.90 | 12.8 |
| 18-112 | Fine weave, sprayed | 66 | 200 | 475 | 0.31 | 5.05 | 9.3 |
| 18-114 | Fine weave, sprayed | 48 | 200 | 475 | 1.35 | 4.24 | 10.6 |
| 18-116 | Fine weave, sprayed, cone shape | 40 | 200 | 475 | 0.25 | 2.18 | 4.9 |
| 18-118 | Fine weave, sprayed | 48 | 200 | 475 | 1.37 | 6.99 | 14.1 |
| 18-123 | Fine weave, sprayed, wide opening | 48 | 200 | 475 | 0.55 | 3.51 | 17.8 |
| 18-135 | Fine weave, painted | 48 | 200 | 475 | 0.69 | 7.69 | 16.3 |
| 18-142 | Fine weave, painted | 36 | 200 | 475 | 0.43 | 5.28 | 11.2 |
| 18-146 | Coarse weave, painted, larger bag | 36 | 200 | 475 | 0.66 | 7.42 | 19.3 |
| 18-149 | Fine weave, painted | 18 | 200 | 475 | 1.12 | 6.15 | 19.1 |
| 18-154 | Fine weave, painted | 36 | 200 | 475 | 1.09 | 6.04 | 18.8 |
| 18-157 | Silicon carbide cloth | 18 | 200 | 475 | 0.70 | 5.14 | 16.0 |
| 18-167 | Steel sheet | 18 | 200 | 475 | 1.04 | 6.70 | 20.8 |
| 18-168 | Steel sheet | 18 | 200 | 475 | 1.06 | 7.08 | 22.0 |
| 18-170 | Steel fabric | 18 | 200 | 475 | 0.95 | 6.41 | 19.9 |

Fig. 4

Table 3. Overview of Regeneration Test Results in the 7.5 cm OD Test Stand

| Test Number | Sample Description | Time (hrs) | Gas Flow (sccm) | T (°C) | C Rate (g/gcat/hr) | C Rate (mg/cm²/hr) | Carbon Yield (%) |
|---|---|---|---|---|---|---|---|
| 18-135 | Fine weave, painted | 48 | 200 | 475 | 0.69 | 7.69 | 16.3 |
| - | carbon removed, re-reun | 11 | 200 | 475 | 0.30 | 3.33 | 7.0 |
| - | carbon removed, re-reun | 18 | 200 | 475 | 0.40 | 4.44 | 9.4 |
| 18-146 | Coarse weave, painted, larger bag | 36 | 200 | 475 | 0.66 | 7.42 | 19.3 |
| - | carbon removed, re-reun | 18 | 200 | 475 | 0.44 | 4.93 | 12.8 |
| 18-149 | Fine weave, painted | 18 | 200 | 475 | 1.12 | 6.15 | 19.1 |
| - | carbon removed, re-reun | 18 | 200 | 475 | 0.96 | 5.22 | 16.2 |
| - | carbon removed, re-reun | 18 | 200 | 475 | 0.49 | 2.67 | 8.3 |
| - | carbon removed, infiltrated | 18 | 200 | 475 | 0.73 | 6.18 | 19.2 |

Fig. 5

Table 4. Hydroxide Catalyst Suspension Tests

| Test Number | Sample Description | Time (hrs) | Gas Flow (sccm) | T (°C) | C Rate (g/g$_{cat}$/hr) | C Rate (mg/cm$^2$/hr) | Carbon Yield (%) |
|---|---|---|---|---|---|---|---|
| 18-193 | Nitrates, binder, on steel sheet | 18 | 200 | 475 | 1.29 | 6.71 | 20.9 |
| 18-194 | Nitrates, thickener, on steel sheet | 18 | 200 | 475 | 1.37 | 6.40 | 19.9 |
| 18-197 | Hydroxides, binder, thickener, on sheet | 18 | 200 | 475 | 1.32 | 6.89 | 21.4 |
| 18-197 | Hydroxides, binder, thickener, on sheet | 18 | 200 | 475 | 1.32 | 6.89 | 21.4 |
| 31-19 | Hydroxide spray | 18 | 200 | 475 | 1.35 | 5.72 | 17.8 |
| 31-23 | Hydroxide spray, higher loading | 18 | 200 | 475 | 1.41 | 7.27 | 22.6 |

Fig. 6

Table 5. Mass of Degradation Coupons as a Function of Cycle Number

| Cycle Number | SS-316 Sheet Weight (g) | Copper Sheet Weight (g) |
|---|---|---|
| 1 | 10.413 | 6.861 |
| 2 | 10.410 | 6.865 |
| 3 | 10.410 | 6.862 |
| 4 | 10.417 | 6.864 |
| 5 | 10.416 | 6.859 |
| 6 | 10.416 | 6.869 |
| 7 | 10.416 | 6.868 |
| 8 | 10.417 | 6.870 |
| 9 | 10.419 | 6.874 |
| 10 | 10.417 | 6.875 |

Fig. 7

Table 6. Adhesion Testing Results Demonstrating Carbon Coat Weight

| Run | Coating Mix by Weight | Anhydrous Catalyst Loading (mg/cm2) | Total Coat Weight Before Test | Total Coat Weight After Test | Total Carbon Weight After Test |
|---|---|---|---|---|---|
| 31-32-A | 90% $Fe_{0.5}Co_{0.5}(OH_3)$/ 10% Cornstarch | 5.13 | 0.143 | 0.032 | 0.393 |
| 31-34-A | 80% $Fe_{0.5}Co_{0.5}(OH_3)$/ 20% Cornstarch | 5.43 | 0.170 | 0.067 | 0.369 |
| 31-34-B | 70% $Fe_{0.5}Co_{0.5}(OH_3)$/ 30% Cornstarch | 5.17 | 0.185 | 0.191 | 0.786 |
| 31-32-B | 60% $Fe_{0.5}Co_{0.5}(OH_3)$/ 40% Cornstarch | 3.78 | 0.157 | 0.303 | 0.646 |
| 31-32-C * | 90% $Fe_{0.5}Co_{0.5}(OH_3)$/ 10% PAA | 5.41 | 0.138 | 0.006 | 0.355 |
| 31-32-D | 60% $Fe_{0.5}Co_{0.5}(OH_3)$/ 40% PAA | 4.88 | 0.206 | 0.021 | 0.757 |
| 31-37-A | 70% $Fe_{0.5}Co_{0.5}(OH_3)$/ 30% Ferrous Acetate | 5.66 | 0.203 | 0.041 | 0.434 |
| 31-37-B ** | 100% Ferrous Acetate | 5.16 | 0.129 | 0.019 | 0.292 |
| 31-40 | 70% $Fe_{0.5}Co_{0.5}(OH_3)$/ 30% Methyl Cellulose | 4.95 | 0.178 | 0.063 | 0.677 |

\* 31-32-C fell from ceramic dish and lost some coating before being weighed

\*\* 31-37-B weigh boat fell as it was removed from reactor and potentially lost coating before being weighed

Fig. 8

Table 7. Summary of Test Results for 15-cm OD Alpha-Prototype Reactor Testing

| Test Number | Sample Description | Time (hrs) | Gas Flow (sccm) | T (°C) | C Rate (g/gcat/hr) | C Rate (mg/cm$^2$/hr) | Carbon Yield (%) |
|---|---|---|---|---|---|---|---|
| 18-156 | Fine weave carbon cloth | 18 | 2200 | 475 | ~0.81 | 4.06 | 13.7 |
| 18-159 | Fine weave carbon cloth | 18 | 2200 | 475 | 0.84 | 4.44 | 15.0 |
| 18-161 | Fine weave carbon cloth | 18 | 2200 | 475 | 0.74 | 5.35 | 17.1 |
| 18-162 | Fine weave carbon cloth | 18 | 2200 | 475 | 0.80 | 6.48 | 18.9 |
| 18-163 | Fine weave carbon cloth | 93 | 2200 | 475 | 0.55 | 4.30 | 13.0 |
| 18-173 | Steel sheet | 79 | 2200 | 475 | 0.12 | 3.90 | 13.0 |
| 18-179 | Steel sheet w/ regens | 68 | 2200 | 475 | 0.34 | 6.26 | 21.0 |
| 18-182 | Steel sheet w/ infiltrate | 100 | 2200 | 475 | 0.43 | 1.98 | 6.6 |
| 18-187 | Steel sheet w/ infiltrate | 104 | 2200 | 475 | 0.41 | 5.10 | 12.9 |
| 18-199 | Steel sheet, single infiltr. | 100 | 2200 | 475 | 1.27 | 6.52 | 16.6 |

Fig. 10

Table 8. Summary of Test Results for Beta-Prototype Reactor Testing

| Test Number | Sample Description | Time (hrs) | Gas Flow (sccm) | T (°C) | C Rate (g/g$_{cat}$/hr) | C Rate (mg/cm$^2$/hr) | Carbon Yield (%) |
|---|---|---|---|---|---|---|---|
| 31-004 | Hydroxide, hand spray | 25 | 2200 | 475 | 1.22 | 6.27 | 16.0 |
| 31-015 | Hydroxide, nozzle spray | 17 | 2200 | 475 | 0.98 | 4.06 | 10.3 |
| 31-024 | Hydroxide, nozzle spray | 100 | 2200 | 475 | 0.73 | 4.83 | 12.3 |
| 31-042 | Hydroxide, nozzle spray | 130 | 2200 | 475 | 1.00 | 5.84 | 14.9 |
| 31-045 | Hydroxide, atomized | 87 | 2200 | 475 | 0.57 | 6.86 | 17.0 |
| 31-057 | Hydroxide, atomized | 27 | 2200 | 475 | 1.33 | 4.17 | 10.6 |
| 31-061 | Hydroxide, atomized | 104 | 2420 | 475 | 0.68 | 4.27 | 10.9 |
| 31-066 | Hydroxide, atomized | 50 | 2200 | 475 | 0.97 | 6.49 | 16.5 |
| 31-075 | Hydroxide, atomized | 40 | 2200 | 475 | 0.80 | 4.91 | 12.5 |
| 31-081 | Hydroxide, atomized | 144 | 2173 | 475 | 0.67 | 3.70 | 9.4 |
| 31-084 | Hydroxide, no liner | 46 | 2660 | 475 | 0.76 | 4.77 | 6.9 |
| 31-088 | Hydroxide, no liner | 35 | 2350 | 475 | 1.39 | 6.67 | 15.9 |

Fig. 13

Gas composition throughout the duration of test 31-42.

Reactor pressure during run 31-42.

Fig. 16  Product gas results of steel liner coated in-situ after carbon removal; run 31-45.

Dry product gas composition from test 31-081.

Product gas composition from test 31-088.

Layout for a 4-CM flight system.

P&ID of the CFR unit for a 4-CM flight system.

CARBON FORMATION REACTOR AND METHOD OF USING SAME

CROSS-REFERENCE TO RELATED APPLICATIONS

This application claims the benefit of U.S. Provisional Patent Application 62/364,468 filed Jul. 20, 2016.

STATEMENT REGARDING FEDERALLY SPONSORED RESEARCH OR DEVELOPMENT

This invention was made with government support under National Aeronautics and Space Administration Contract Number NASA NNC15CA03C. The government may have certain rights in the invention.

TECHNICAL FIELD

The present disclosure relates generally to a method for making a carbon formation reactor, and a method for using the same.

BACKGROUND OF THE INVENTION

For manned space flights (and other applications requiring life-support systems) it is desirable to recover oxygen from the carbon dioxide exhaled by the crew. This can be partially achieved with electrolysis (water or carbon dioxide electrolysis) and/or reverse water gas shift reactors, which convert carbon dioxide to carbon monoxide. However, an additional "carbon formation" process step is required to convert carbon monoxide to solid carbon, allowing the system to recover all of the oxygen. For example, carbon monoxide can be reduced to solid carbon via the Boudouard reaction shown below:

$$CO + CO \leftrightarrow CO_2 + C_{(s)}$$

The following disclosure reveals a reactor design based on a catalyst coatings approach that can significantly reduce the size, mass, and/or catalyst consumption costs of carbon formation reactors compared to previous approaches, for example, as reported in Holmes, R. F., E. E. Keller, and C. D. Kilzg, *A Carbon Dioxide Reduction Unit Using Bosch Reaction and Expendable Catalyst Cartridges*, NASA Report, Contract NAS 1-8217. For a one Crew Member (CM) reactor (272 g/day of carbon), the disclosed reactor core is <8 kg mass with and <10 L volume. The reactor resupply is <1 kg/year/CM, with regeneration frequency >24 hours. For a possible 1-CM CFR design of 20 cm OD by 30 cm L, the size and mass would be 9.4 L, <4 kg. Based on 2,200 $cm^2$ available coating area in the design, catalyst activity of at least 5 $mg_{carbon}/cm^2/hr$ is required to make sufficient carbon for 1 CM (272 g/day). This provides an activity target for catalyst testing. Further based on a target 5 $mg/cm^2$ of catalyst loading, the catalyst must last 97 hours before replacement for resupply to be <1 kg/year. Catalyst testing examples described below reveal examples of catalysts that can meet these requirements. In some examples catalyst coatings were deposited on light-weight woven carbon cloth. However, as will be discussed, catalyst can be coated on a number of other substrate surfaces, including steel, copper, or quartz. Additionally, carbon cloth can be used as a "filter" media at the reactor exit to retain the formed carbon and catalyst. The disclosed invention may also find use in terrestrial applications including carbon sequestration systems and manufacturing of carbon nanomaterials. Further, it is expected that the catalysts and reactor design could generate carbon from nearly any non-oxidizing gas stream that contains carbon.

SUMMARY OF THE INVENTION

The following disclosure reveals a reactor design based on a catalyst coatings approach that can significantly reduce the size, mass, and/or catalyst consumption costs of carbon formation reactors compared to previous approaches. The carbon formation process as described refers to the formation of solid carbon from a gaseous stream, however, one skilled in the art will realize that the reactor and method could be applicable to any fluidic stream.

BRIEF DESCRIPTION OF THE ILLUSTRATIONS

Without limiting the scope of the carbon formation reactor as disclosed herein and referring now to the drawings and figures:

FIG. 2 shows "Table 1. Initial Substrate Tests;"

FIG. 3*a* shows examples of test configurations at the 7.5 cm OD scale;

FIG. 3*b* shows further examples of test configurations at the 7.5 cm OD scale;

FIG. 3*c* shows further examples of test configurations at the 7.5 cm OD scale;

FIG. 4 shows "Table 2. Overview of Single-Cycle Test Results in the 7.5 cm OD Test Stand;

FIG. 5 shows "Table 3. Overview of Regeneration Test Results in the 7.5 cm OD Test Stand;

FIG. 6 shows "Table 4. Hydroxide Catalyst Suspension Tests;"

FIG. 7 shows "Table. 5. Mass of Degradation Coupons as a Function of Cycle Number;"

FIG. 8 shows "Table 6. Adhesion Testing Results Demonstrating Carbon Coat Weight;"

Figure 9:
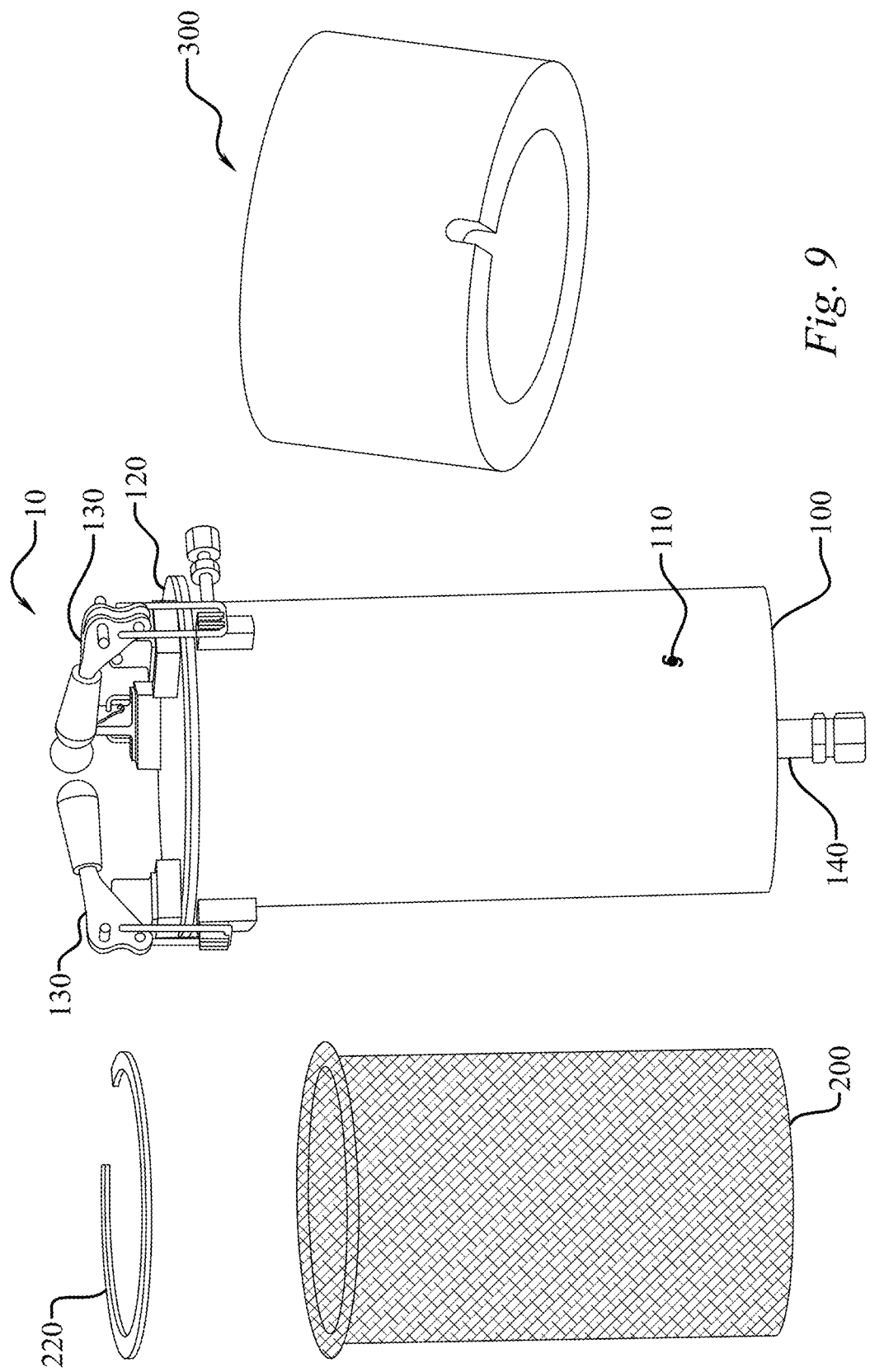

FIG. 9 shows a prototype carbon formation reactor according to one embodiment of the instant invention;

FIG. 10 shows "Table 7. Summary of Test Results for 15 cm OD Alpha-Prototype Reactor Testing;"

Figure 11:
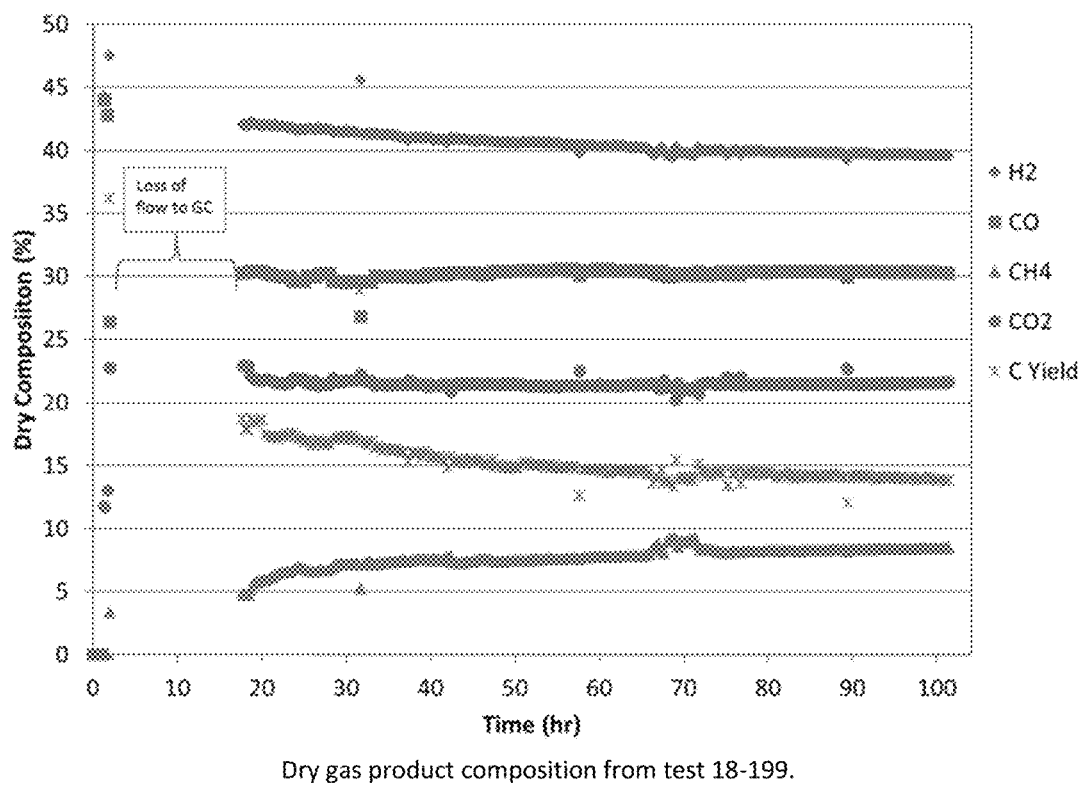
Figure 12:
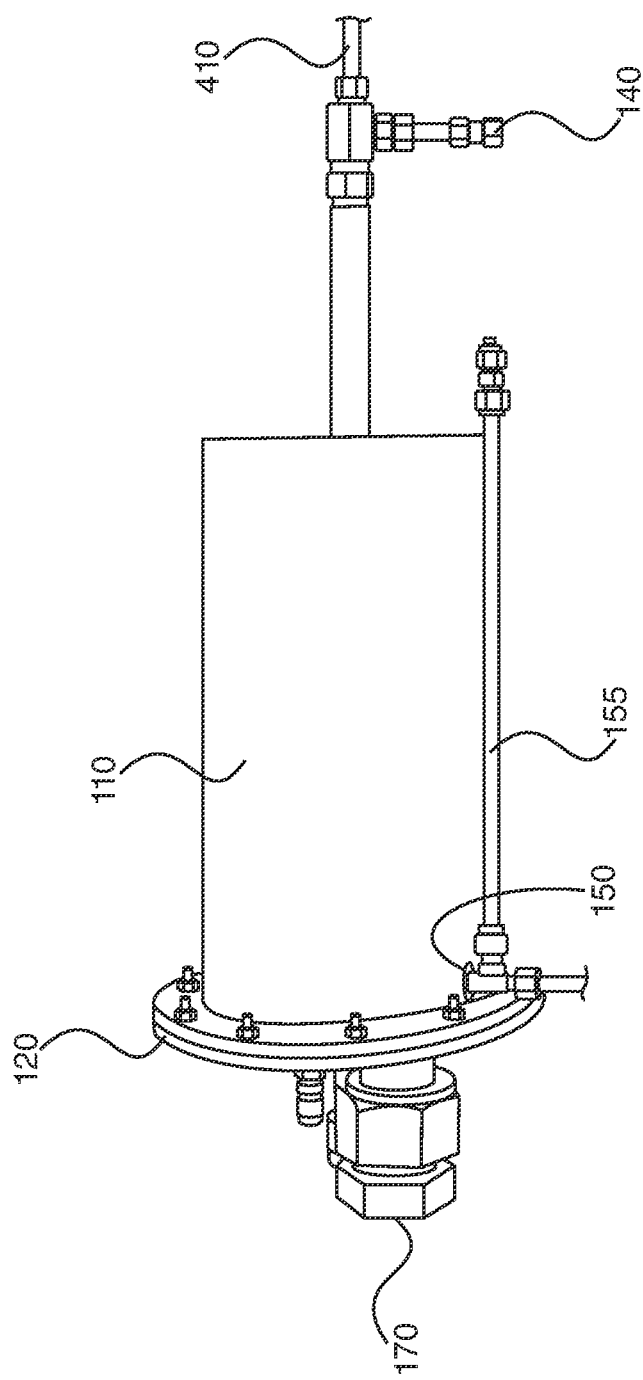

FIG. 11 shows dry gas product composition from Test 1-199 (FIG. 10; Table 7);

FIG. 12 shows a photograph of a carbon formation reactor according to one embodiment of the instant invention;

FIG. 13 shows "Table 8. Summary of Test Results for Beta-Prototype Reactor Testing;"

Figure 14:
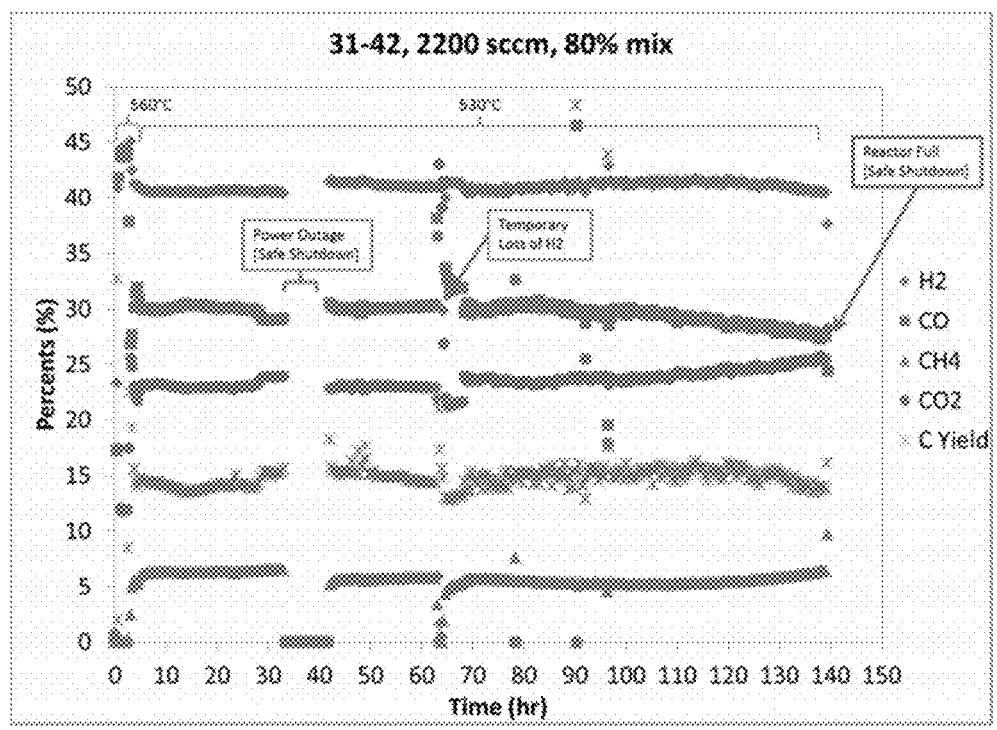
Figure 15:
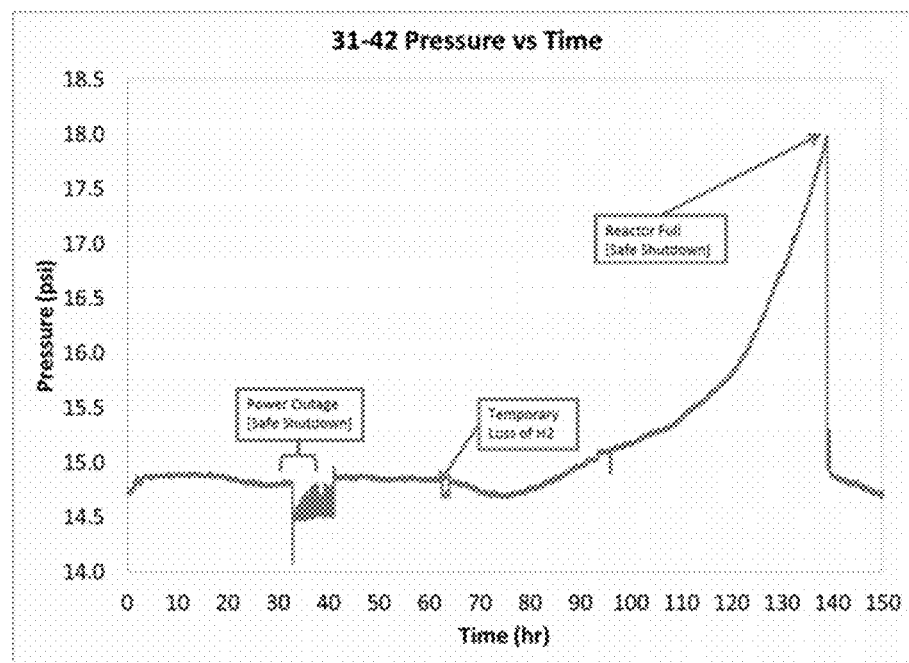
Figure 16:
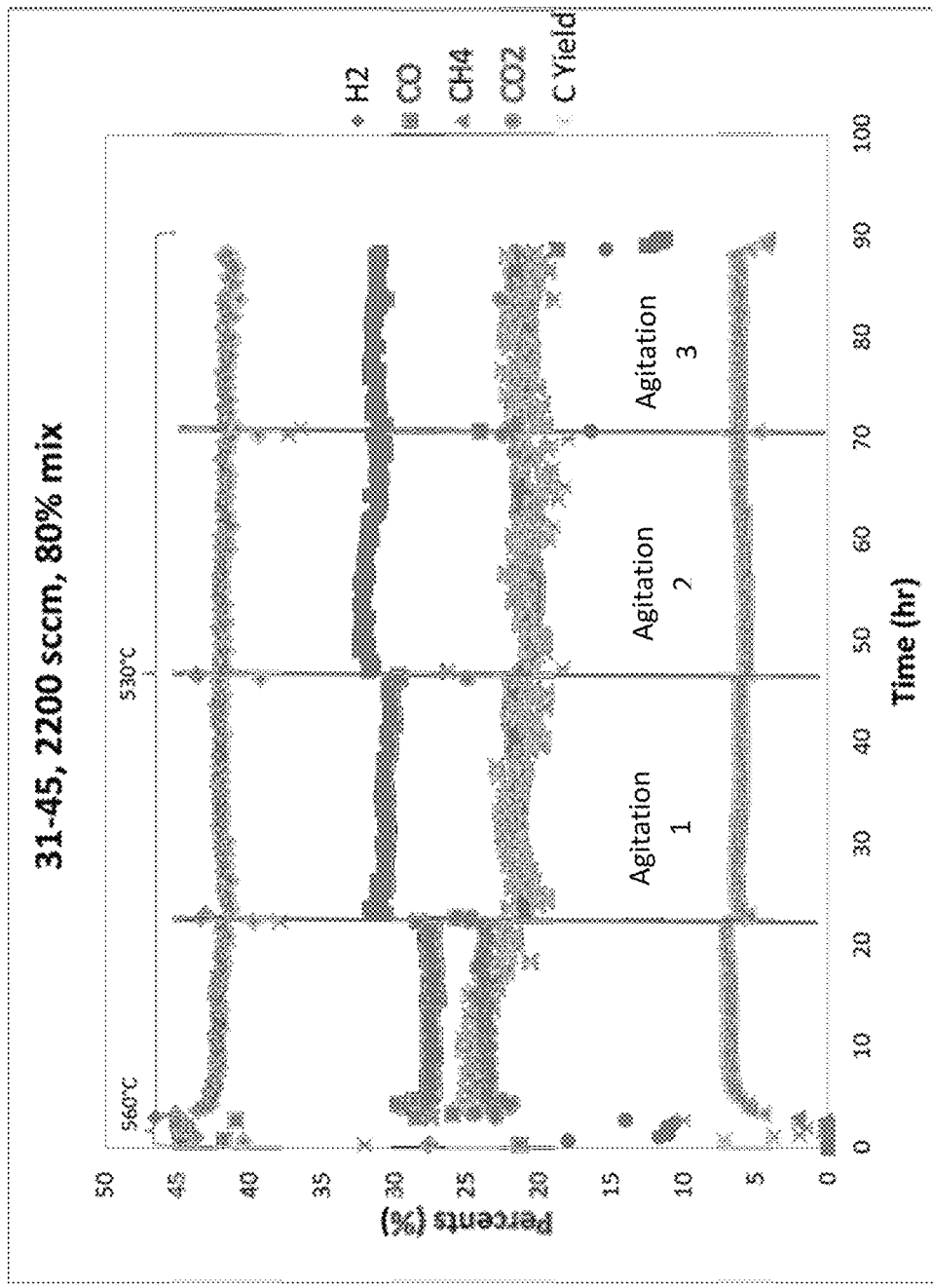
Figure 17:
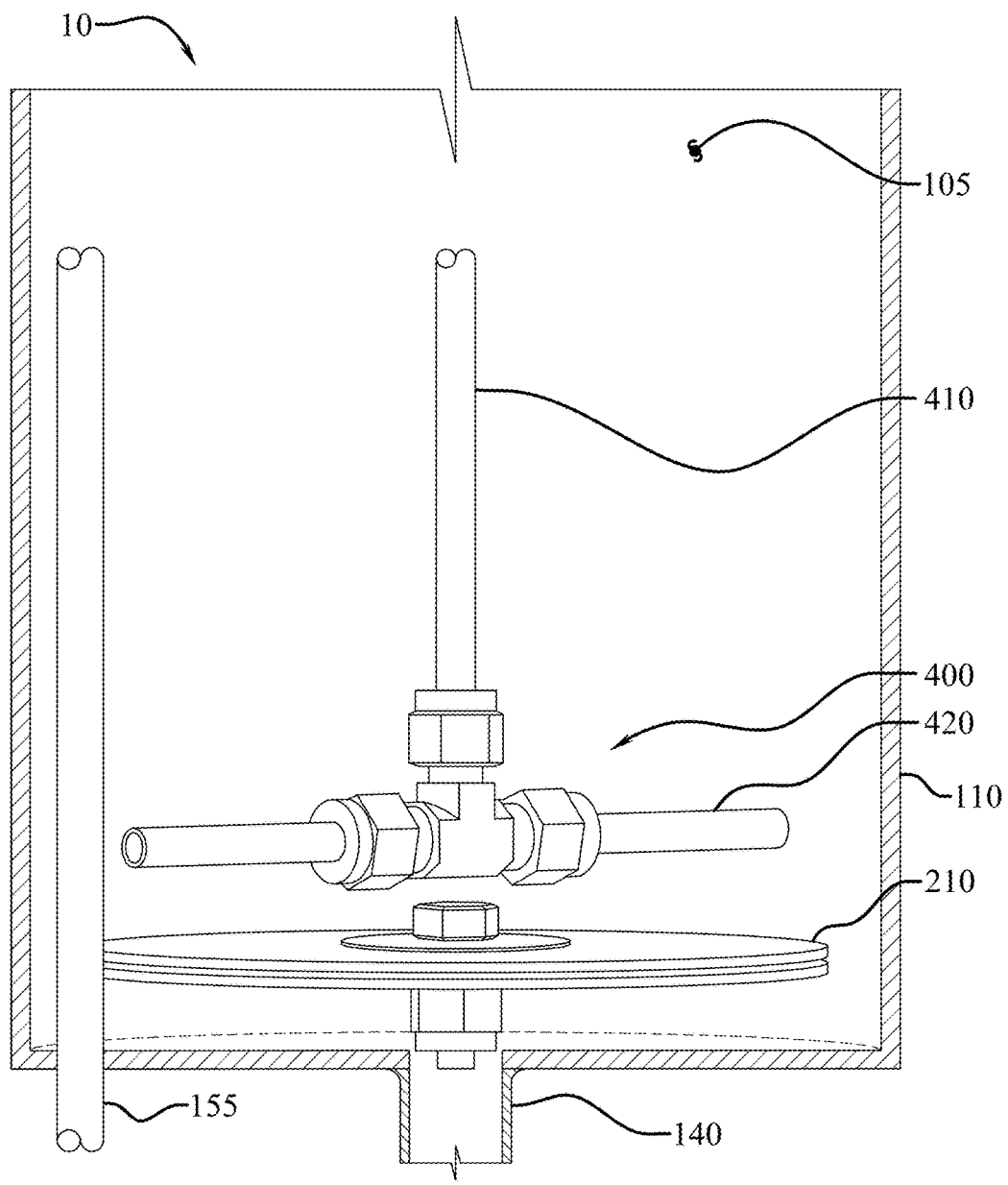
Figure 18:
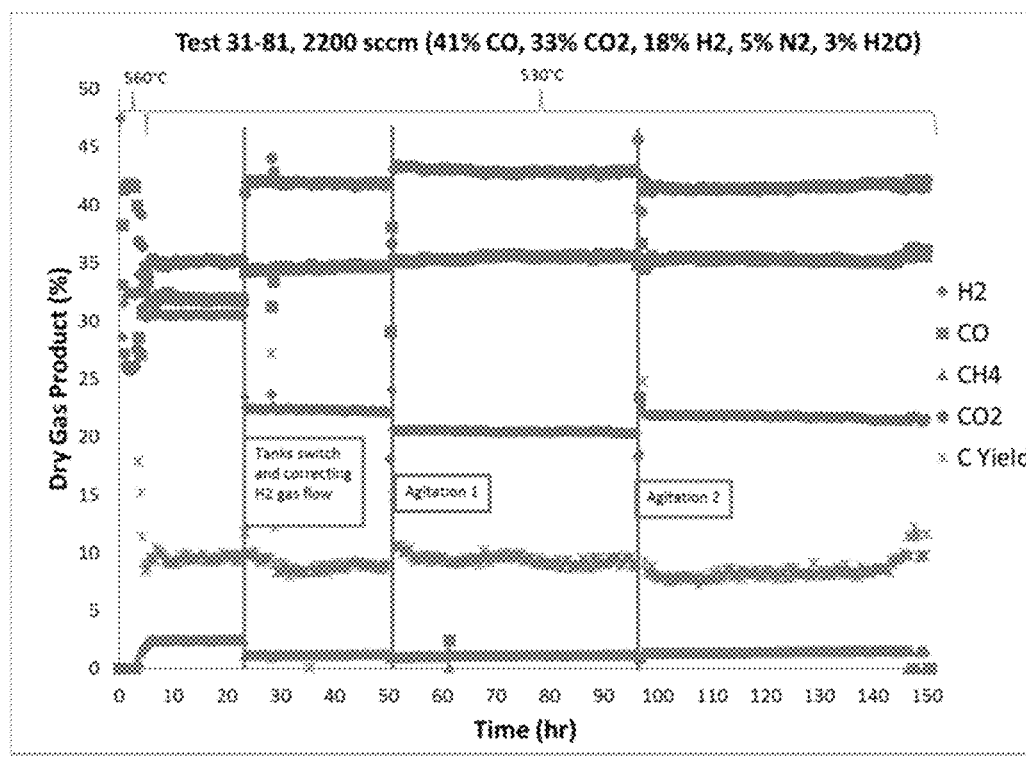
Figure 19:
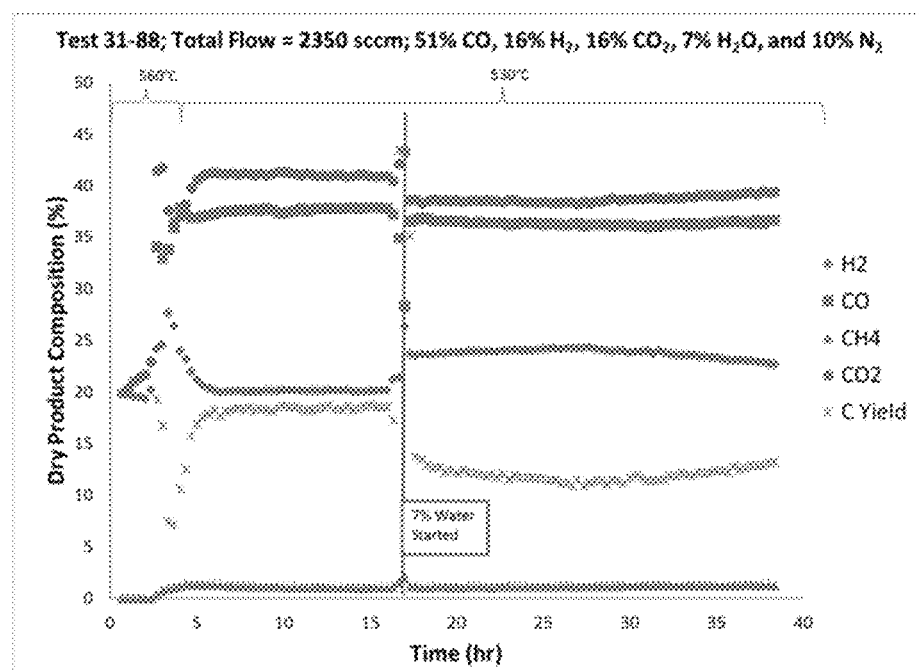
Figure 20:
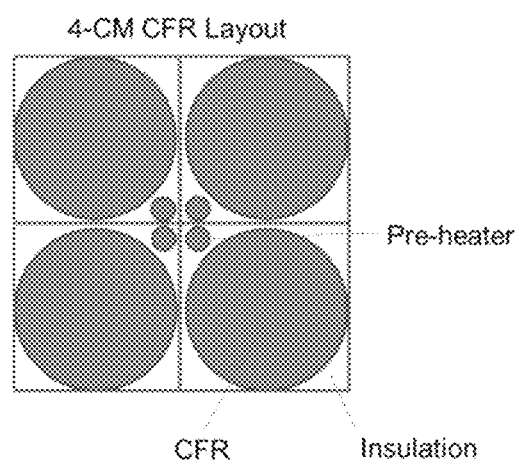
Figure 21:
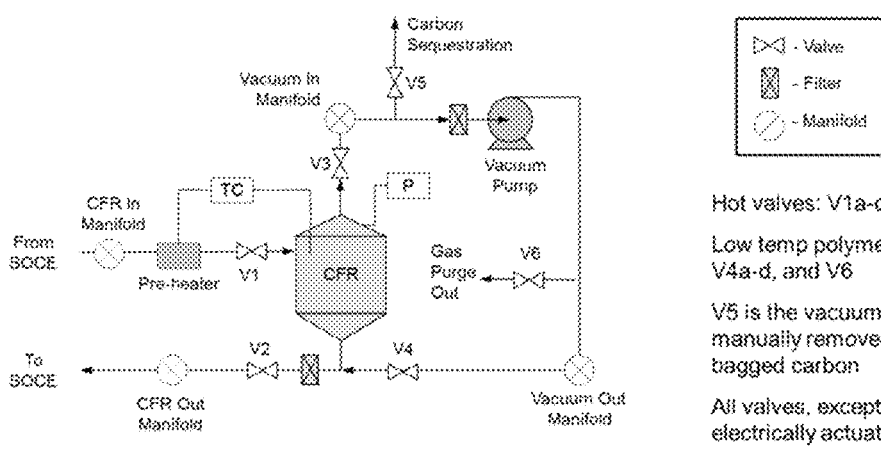
Figure 22B:
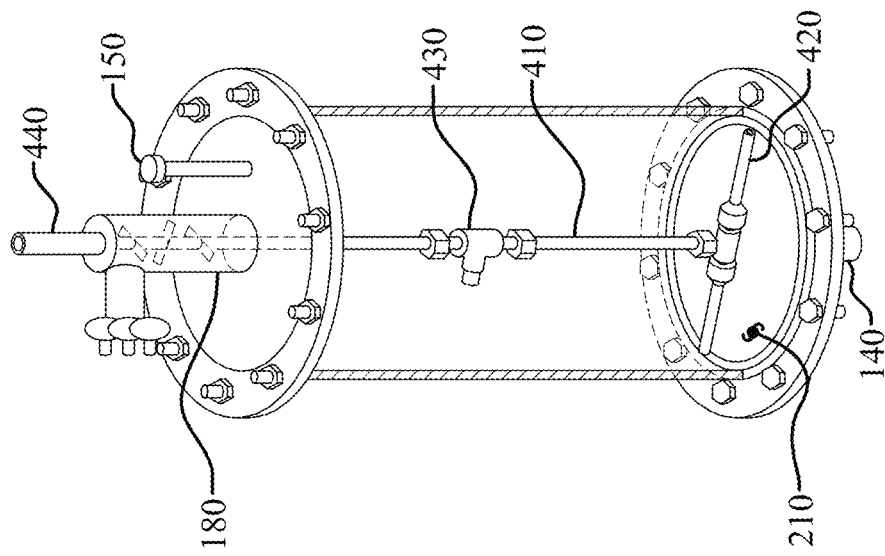
Figure 22A:
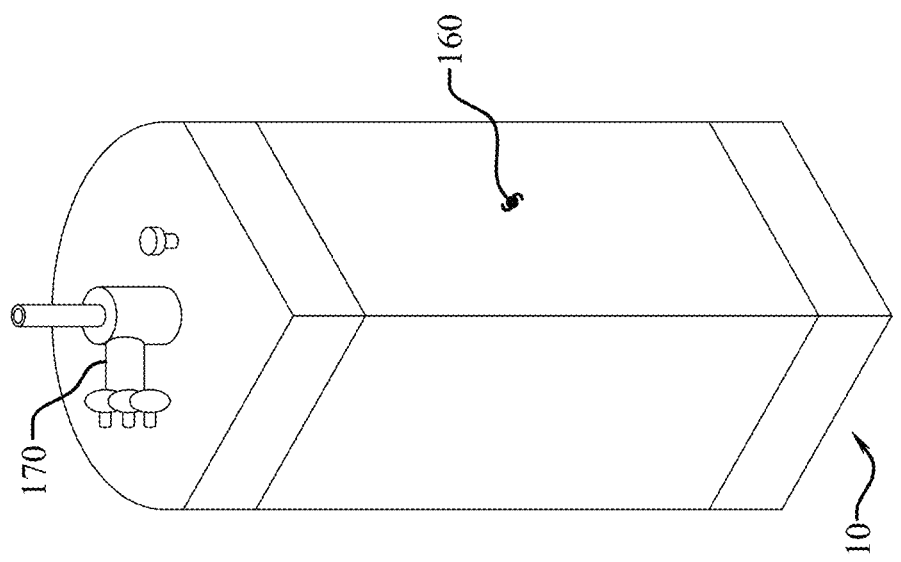

FIG. 14 shows gas composition throughout the duration of Test 31-042 (FIG. 13; Table 8);

FIG. 15 shows reactor pressure during Test 31-042 (FIG. 13; Table 8);

FIG. 16 shows product gas results of steel liner coated in-situ after carbon removal Test 31-045 (FIG. 13; Table 8);

FIG. 17 shows a cross sectional view of another embodiment of a carbon formation reactor according to one embodiment of the instant invention;

FIG. 18 shows dry product gas composition from Test 31-081 (FIG. 13; Table 8);

FIG. 19 shows product gas composition from Test 31-088 (FIG. 13; Table 8);

FIG. 20 shows one embodiment of a layout for a 4-CM flight system;

FIG. 21 shows a P&ID of one embodiment of the CFR unit for a 4-CM flight system;

FIG. 22a shows an external structural view of another embodiment of a carbon formation reactor according to one embodiment of the instant invention; and FIG. 22b shows an internal structural view of another embodiment of a carbon formation reactor according to one embodiment of the instant invention.

These illustrations are provided to assist in the understanding of the exemplary embodiments of a carbon formation reactor, and a method for using the same, as described in more detail below, and should not be construed as unduly limiting the specification. In particular, the relative spacing, positioning, sizing and dimensions of the various elements illustrated in the drawings may not be drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

Examples of CFR Test Results 2.5-cm Test Results.

Figure 1:
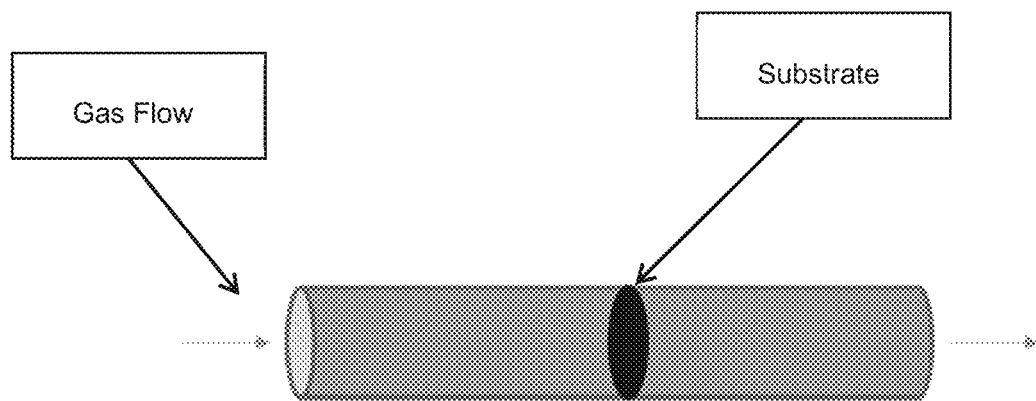
FIG. 1 shows a schematic diagram of the 2.5 cm OD reactor test configuration.

A 2.5-cm OD reactor was set-up to test 5-$cm^2$ catalyst-coated carbon cloth discs mounted perpendicular to the gas flow (see FIG. 1). This configuration was designed to eliminate any mass transfer/flow uniformity issues. The purpose of the reactor was to allow fast throughput of testing for the catalyst, support, and feed conditions. Tests were run typically run overnight for 18 hours at temperature with a gas chromatograph measuring the dry product composition every 20 minutes. The standard conditions for this testing, unless otherwise specified, are listed below:
1) Tests ran 18 hours with GC injections every 20 minutes;
2) Feed gas of 44% CO, 44% $H_2$, 12% $CO_2$, flow rate of 10 sccm unless otherwise specified;
3) Operating temperature of 475° C., unless otherwise specified; and
4) A solution of 10:10:1 by mass mixture of iron nitrate: cobalt nitrate: Sekisui BL-1 binder dissolved in water was used to coat the samples prior to testing unless otherwise specified.

A number of variables were tested, including:
1) Catalyst composition and loading;
2) Catalyst support (type of cloth and microporous carbon coating);
3) Flow rate;
4) Gas composition;
5) Temperature; and
6) Pre-treatment conditions.

An overview of test results is shown in FIG. 2 (Table 1). The mass of carbon formed was determined after each test using a laboratory scale. The growth rate of solid carbon is reported on a catalyst mass and coating area basis, as well as the carbon yield (the mass of carbon formed directly determined by weight divided by the mass of carbon that is fed to the reactor based on gas flows).

Experimental test runs 18-26 to 18-113 (shown in FIG. 2 (Table 1)) identified the following:
1) Optimal temperature was identified as 475° C.;
2) High performance was obtained in humidified gas streams (18-80, 18-82);
3) The best-performing catalysts have some methane selectivity. It is not believed that methane would build up in a closed system with a recycle loop because its product composition is equilibrium limited;
4) Based on GC analysis (data not shown) the product gas composition was fairly stable once the operating temperature is reached, and the product gas clears out the downstream part of the system. This indicates that the growth rate is not aided by initial high activity, and can continue to produce carbon for a longer time;
5) Some increase in CO product is observed as the test proceeds, likely indicating one of two phenomena: (1) the catalyst may have a slow degradation mechanism, or (2) as the pressure drop across the cloth increases with increases carbon deposits, a higher percentage of the gas circumvents the cloth around the edges, which are not sealed to the reactor walls;
6) The catalyst can be supported effectively either directly on the carbon cloth, or on cloth that is pre-coated with microporous carbon nanofibers. Directly on the cloth has an advantage of being easier to ship and store. However, the direct cloth approach requires reduction using the gas feed at 550° C. that can be done either in situ or externally to obtain higher catalytic performance. It is believed that the reduction step may convert the catalyst component from a nitrate to a more active alloy and/or carbide phase;
7) Fe/Co consistently has about 2× higher growth rates than iron. Both make 5-10% methane (dry composition). The nitrate form worked better than pre-reduced metallic particles; and
8) Carbon yield of 15-17% was repeatedly obtained under standard test conditions at the target growth rate. Higher carbon yield of 30.3% was obtained at lower flow rate (see FIG. 2 (Table 1); Test 18-68), but the rate is lower than the target for this condition. 9) Higher flow rates give better activity at the expense of conversion (50 to 3 sccm flows examined); this means a smaller reactor could be designed, but it would require a higher recycle ratio if using a closed system.

A number of gas compositions were examined in testing. As the CFR could be integrated into systems with various design approaches. Consequently, catalyst-coated cloths were tested under a range of gas compositions. For example, the standard gas composition consisting of 40% CO, 40% $H_2$, 10% $CO_2$ and 10% $N_2$ is representative of the predicted dry product stream from a Solid-Oxide Co-Electrolysis (SOCE) unit with 80% carbon dioxide conversion. A gas composition of 35% CO, 51% $H_2$ and 15% $CO_2$, more closely representing 70% SOCE conversion was tested and demonstrated above target carbon formation (see FIG. 2 (Table 1); Test 18-93). The exhaust from an SOCE is anticipated to contain ~10% water. Knockout of water from the gas stream using a condenser prior to entering the carbon formation reactor may improve reactor performance, but may not be required. Removing water from the gas stream would likely increase the mass of the system.

Accordingly, tests were also run to evaluate performance when water is present in the gas stream. Humidification of the gas stream was completed using a simple water bubbler immediately adjacent to the reactor inlet. The extent of humidification was controlled via bubbler temperature and a benchtop controller. Tests were run at 10% humidification, corresponding to 80% SOCE conversion up to 19% humidification, corresponding to 70% SOCE conversion. The results of the testing are shown in FIG. 2 (Table 1), Tests 18-80 and 18-82. Performance of the carbon formation reactor exceeded the target carbon formation rate of 5 $mg/cm^2/hr$ for both tests, although carbon formation was slightly less at the higher humidification. Furthermore, in comparison to non-humidified tests operating under similar conditions, there is little evidence that water in the feed stream has a significant effect on the catalyst performance for pre-reduced catalysts. This is an important result as it would eliminate the need for a condenser, reducing the system mass.

Maximizing the catalyst lifetime and minimizing operator time will greatly reduce the equivalent system mass (ESM). Accordingly, tests were conducted on the 2.5 cm platform investigating the life of the carbon fiber cloth and catalyst. Testing demonstrated performance stability over 100 hours while operating at 10 sccm (see FIG. 2 (Table 1); Test 18-84). This result was significant because it showed extended continuous catalyst operation. The carbon mass gain was 34 times higher than the catalyst/cloth, and based on GC data, the cloth still had activity when the test was stopped. The average activity was 22% lower than typical, so more testing is needed to determine if carbon formation declines with time. Possible explanations are that the catalyst activity may drop over time, feed gas may bypass the catalyst as pressure drop increases with carbon deposition, or the result was due to test-to-test variations.

A series of tests also examined the effect of temperature. At temperatures below 425° C. the target carbon formation rate was not achieved; however, the loss in performance is mild until below about 350° C. (see FIG. 2 (Table 1); Tests 18-86, 89, 90, 95).

7.5-cm Test Results.

A 7.5-cm OD CFR test bed was constructed to test three-dimensional catalyst substrates. Three configurations were used for this testing: (1) woven carbon fiber cloth bags with a fixed collar, (2) woven carbon cloth bags strapped to the outside of an inlet tube, and (3) flat stainless steel sheets. A drawing of the copper collar configuration is shown in FIG. 3a. Copper was chosen because of its machinability and resistance to carbon formation. The removable copper collar, which is sealed to the wall with an alumina fiber gasket, allows the substrate cloth to be easily removed and weighed after tests. The collar and carbon cloth is loaded into a 7.5 cm diameter quartz furnace, and fed using the same system used for 2.5 cm reactor testing. In the second approach examined, the inlet tube was extended into the quartz furnace and carbon cloth substrate bags were strapped to the end of the tube (see FIG. 3b). This approach was examined to eliminate issues with gas potentially bypassing the cloth. This approach was also easier to load than the initial copper collar design. Finally, flat 100-cm$^2$ stainless steel substrate sheets coated with catalyst were examined. FIG. 3c depicts the orientation of the sheets for this testing.

Beyond just sample activity, tests at this scale examined long-term performance, regeneration tests, and mechanical durability of the support. Variables that were examined included:
1) Type of substrate (carbon cloth, stainless sheet, etc.);
2) Shape of the substrate (L:D ratios, flat plate);
3) Painting versus spraying of the catalyst coating; and
4) Hydroxide versus nitrate catalyst precursor.

FIG. 4 (Table 2) and FIG. 5 (Table 3) summarize the results of 7.5-cm OD testing, and the details are discussed in the following paragraphs. Key results from the 7.5-cm OD testing included:
1) Using 3:2 dimension ratio improved performance of cloth bags;
2) High activity could be obtained with either painting or spraying of the catalyst coating;
3) Flat steel sheets performed as well as cloth bags;
4) Regenerations worked better if catalyst was added after carbon removal; and
5) Mechanical problems with coated carbon cloth bags or steel cloth bags after several cycles were observed, but no mechanical problems were observed with stainless steel plates.

Testing began with a focus on matching the activity of the 2.5-cm tests. All tests incorporated about 100 square centimeters of coated material, an area increase of >20× compared to the 2.5-cm test examples. Most tests were run by strapping carbon cloth tubes around a 2.5-cm steel tube fitting. The furnace design was updated for test 18-106 (FIG. 4; Table 2)(and all subsequent tests), and activity improved to within 50% of the target. The furnace improvements included extension of the heated zone to 15 cm, and addition of radiation shields to improve temperature uniformity at the end of the reactor tubes. In test 18-112 (FIG. 4; Table 2) a shorter bag was examined, with a D:L of approximately 1:1. With the shorter sleeve, high activity per area was achieved; however, with the smaller area than previous tests, the carbon yield was lower than 10%. Next, a D:L ratio of 3:2 was examined in test 18-114 (FIG. 4; Table 2). Area-based activity was just below the target, but yield improved in this test. In test 18-116 (FIG. 4; Table 2), a cone-shaped cloth was examined; however, activity was poor. In test 18-118 (FIG. 4; Table 2), it was decided to evaluate an alternative extended purge/reduction. In this test, the reactor was purged for 18 hours before initiating the reduction. The improved purge had a significant impact, as activity reached 6.99 mg/cm$^2$/hr. The conditions for test 18-118 and 18-114 (FIG. 4; Table 2) are identical, except for the longer purge. It should also be noted for this test, the product carbon density (based on the mass produced and bag volume) was 0.45 g/cm$^3$. Consequently, the longer purge was adopted in the SOP and used in all subsequent testing. In test 18-123 (FIG. 4; Table 2), a larger area was examined, and the cloth was attached to the reactor wall with a retainer ring. Due to the excessive area, the area-based activity was lower, but the carbon yield exceeded 16%. Ideally, one could expect to exceed 5 mg/cm$^2$/hr with 15% single-pass carbon yield. In all of the tests a small percentage (5-10%) of the carbon is found outside the cloth after testing. It is believed that carbon grows on the outside of the bag due to catalyst coating seeping through the bag during the spray coating process. Although this carbon breakthrough can be handled with downstream filters, minimizing breakthrough would minimize filter replacements, thus alternative coating processes were examined.

Thicker catalyst coating formulations were also examined. These thicker formulations allow the catalyst to be painted with a roller onto a single side of the cloth. Both formulations yielded good results, with test 18-135 (FIG. 5; Table 3) producing the highest growth rate per area (7.69 mg/cm$^2$/hr vs. target of 5.0 mg/cm$^2$/hr) in 7.5 cm testing. The formulation for 18-135 (FIG. 5; Table 3) was repeated on a slightly larger coarse weave cloth for test 18-146 (FIG. 5; Table 3). Again, the cloth had high activity, exceeding 7.4 mg/cm$^2$/hr, and the larger cloth obtained the high single-pass carbon yield of 19.3%. Finally, two tests were run with flat cloths instead of bags. The flat cloths were examined to allow more volume for carbon growth, and better represent the optimal full-scale design. The flat cloths were not expected to perform as well because gas is not forced to travel through the cloth, and can thus bypass the catalyst (an effect known as channeling in catalyst beds and filter media). Despite the open configuration, surprisingly both tests (18-149 (FIG. 5; Table 3) and 18-154 (FIG. 4; Table 2)) performed above the target area-based rate. Additionally, the larger clothes nearly matched the best carbon yield of ~19%.

Next, testing switched to a focus on regeneration, and matching the activity target over multiple runs. Tests incorporated 50 to 150 square centimeters (depending on geometry) of coated carbon fiber cloth. Most regeneration tests were run by strapping carbon cloth tubes around a 3.8-cm OD steel fitting, with a coated cloth area that was ~3.8 cm OD by 5.7 cm long, matching the 2:3 ratio of the target design reported above. In some testing, a flat 100-cm$^2$ cloth (14.3 cm by 7.0 cm) coated on one side and laid parallel to the gas flow on a quartz plate was tested. In these tests, carbon was removed from the cloth with gentle brushing and reloaded and run again. In one case, aqueous catalyst solution was used to regenerate the cloth activity. In the first regeneration run, using the cloth from 18-135 (FIG. 5; Table 3), a power outage occurred during the test after 11 hours, cutting off gas flow, which likely lead to poor performance. This cloth was loaded and run again and obtained a growth rate of 4.44 mg/cm$^2$/hr, just below the target. The coarser weave cloth from test 18-146 (FIG. 5; Table 3) was also retested. In the second run the carbon growth was again just below the target, with an area-based rate of 4.93 mg/cm$^2$/hr. In both of these regeneration tests, the carbon density after the second test was higher than the 0.4 g/cm$^3$ target in sections of the bag, and was difficult to separate from the cloth.

Since a larger full-scale design would have more volume for carbon growth, it was decided to test a flat carbon sheet that allows more volume for carbon growth. In this test (18-149) (FIG. 5; Table 3), the carbon product was almost entirely removed from test-to-test. The cloth activity was mostly maintained after the first cycle, but dropped significantly in the next cycle. After the drop in performance, the cloth was infiltrated with aqueous catalyst solution and re-run without any activation treatment. The re-infiltrated cloth returned to its original performance level and achieved 19.2% single-pass carbon yield.

Within the regeneration testing, observations were also made regarding the cloth mechanical durability. The cloths were removed from the reactor and weighed for each run. The cloths held together well after one run, even for the long 48 hour runs; however, they became brittle and more fragile after 2 cycles or more. Based on this result, testing switched focus to alternative supports, such as silicon carbide fabric, woven stainless steel fiber cloth, and stainless steel sheet (see Tests 18-157 through 18-170)(FIG. 5; Table 3).

Overall it was found that all of the catalyst supports performed roughly the same, with activity above the target. However, the woven non-carbon supports suffered the same fate as the carbon cloth, and became brittle during carbon growth. The steel sheet was not affected by the testing other than a change to the surface color. Consequently, the stainless steel sheet catalyst support was used in further testing, and eventually was incorporated into a prototype reactor design, as discussed in the following subsections.

In the final three standard 7.5-cm tests the use of hydroxide catalyst suspension was examined (FIG. 6; Table 4; Tests 18-197, 31-019, and 31-023)[In some of the Tables and in some parts of this Specification, Test runs are denominated with a leading zero ahead of the final two digits, e.g., "31-042" vs "31-42." These are intended to refer to the same Test runs] on the stainless steel sheet support. The hydroxides were prepared by a standard co-precipitation approach. Briefly, iron and cobalt nitrates are dissolved in water then mixed with excess sodium hydroxide, forming insoluble metal hydroxide nano-particles that are washed with excess water, filtered, and dried. The catalysts are then suspended in D.I. water, along with 10% Sekisui BL-1 binder and 10% cornstarch (indicated as thickening agent, although it can acts as both thickening agent and binder) to form a spray mixture.

The hydroxide catalyst was of interest because it contains more metal by mass than nitrate or acetate salts. In each test, a catalyst loading of 5 mg/cm$^2$ (dry solids and binder weight) was targeted on 100-cm$^2$ stainless steel sheets. Identical activation procedures of 1 hours at 550° C. were used for each sample. The first three runs (FIG. 6 (Table 4); Tests 18-193, 18-194, and 18-197) examined whether a commercial binder or a thickening agent (each or which are used to improve the coating process) affected performance. The hydroxides performed just as well as the nitrate coatings. Both samples performed at the same level, within the margin of error.

Tests were also run to examine hydroxide catalyst that was sprayed through a nozzle. In order to spray the catalyst suspension through a nozzle, the catalyst had to be milled using an attrition mill to break up agglomerates, then passed through a fine mesh. There was some concern that the milling step may affect performance. Additionally, the sensitivity of performance to catalyst loading was tested. Run 31-019 (FIG. 6; Table 4) examined the milled catalyst that was applied via a pressurized spray nozzle, simulating a flight system design. The catalyst performed above the target of 5 mg/cm$^2$/hr, but was noticeably less active than previous tests using the same catalyst (unmilled). It is important to note that test 31-019 (FIG. 6; Table 4) had only ~4 mg/cm$^2$ of catalyst, which is below the target of 5 mg/cm$^2$. The lower loading was due to unexpectedly lower yield in the spray process. To determine if the milling or if the lower yield was the cause of the lower performance, test 31-023 (FIG. 6; Table 4) was performed. This new test had the target loading and also used the milled catalyst. The milled catalyst outperformed all previous tests at this scale when the proper loading was used.

Durability Test Results.

There is uncertainty that the desired life of a stainless steel reactor may exceed thousands of hours. It is possible that as carbon grows on the steel walls, small amounts of the steel may be mechanically eroded. The steel may be subject to corrosion, although no evidence during current testing has yet supported this. An attempt was made to determine the rate the steel liner (or CFR wall) will degrade during operation, particularly during carbon removal, heating and cooling, and subsequent sheet infiltration. For this testing a 316 stainless steel sheet, 5 cm×20 cm, was cut from the same stainless steel feedstock used in prototype liners. The sheet was spray-coated with the 5 mg/cm$^2$ target loading of Fe/Co hydroxide catalyst and 30% corn starch as the binder. The sheet was then placed in the 7.5 cm reactor for subsequent testing under standard operating conditions. However, >100 hour long tests would require an extensive amount of time to allow for the number of cycles desired (at least 10). Accordingly, the test procedure was modified so that the sheets could be cycled daily, by reducing the operating time to 18 hours. As a result, sheets were treated at 550° C. for 1 hour followed by 18 hours at 475° C. The gas composition was 40% CO, 40% H$_2$, 10% CO$_2$, and 10% N$_2$ and was run at 200 sccm. Tests were also run with copper sheets for comparison. Copper may be a more appropriate reactor material to avoid long-term degradation. After each cycle, any carbon on the sheets was collected and weighed. The sheet was then wiped cleaned, dried and weighed. A total of 10 cycles were run for each sheet.

FIG. 7 (Table 5) shows the results of degradation testing. Neither the steel sheets nor the copper sheet lost measurable mass during the testing. Visually the sheets showed consistent carbon growth after each test, and both materials grew the same mass of carbon (exceeding the target carbon growth rate) when placed in identical locations within the reactor. The mass of carbon is not shown since the sheet locations in the reactor were not consistent in all tests.

Adhesion Test Results.

In an effort to improve catalyst adhesion and optimize binder loading, a study was performed to test adhesion of the catalyst to the steel liner. Accordingly, several different adhesion agents at different loading levels were assessed on stainless steel coupons. In particular, binders, including cornstarch at 10, 20, 30 and 40% by wt. levels, polyacrylic acid at 10 and 40%, and methyl cellulose at 30%, were evaluated for adhesion. In addition, ferrous acetate, due to its sticky behavior upon drying, was also evaluated as an adhesive agent and as a raw material for the Fe portion of the catalyst. Slurry compositions of each formulation were prepared and sprayed onto metal coupons. Sprays of slurry were applied until the dried coat weight reached the target catalyst loading. The coated coupons were placed vertically into alumina crucibles, held up by steel clips, and placed into the 7.5 cm quartz reactor used previously on this project. The samples were purged with the mixed CFR feed gas for 1 hour before being heat treated to 550° C. for 1 hr, i.e. the standard activation/reduction condition. After firing, the steel sheets were collected, imaged, and weighed to determine the carbon loading on the sheets. The results of this study are summarized in FIG. 8 (Table 6).

The amount of carbon adhered to the steel sheet with 40% cornstarch is much greater than the 10% case. Data from FIG. 8 (Table 6; Test 32-32A vs 31-32B) shows that the 40% cornstarch sample retained 10 times the amount of coating as the 10% case. Furthermore, intermediate loadings, at 20% and 30% cornstarch, had proportional amounts of coating. This supports the belief that catalyst adhesion to the steel sheet is important to maintaining catalyst activity throughout testing.

Optimization of the adhesive agent is critical to reducing the weight of the final catalyst composite needed. Accordingly, other agents, polyacrylic acid and methyl cellulose, were also assessed for performance. Ideally, the best agent would function well at the lowest loading and lead to extensive carbon growth. However, these alternative adhesive agents, according to the results in FIG. 8 (Table 6), did not perform as well as cornstarch coating at similar weights. None of the agents, except cornstarch, were able to adhere more than 100 mg of coating after the test. Accordingly, cornstarch was identified as the best agent for adhering the catalyst to the steel sheet, and the 30% cornstarch loading was identified as having the optimal carbon retention while having minimal weight. This composition was down-selected for the proceeding prototype tests.

15-cm Test Results

Alpha-Prototype Testing. The "alpha-prototype" CFR test bed was initially designed and used to demonstrate activity and regeneration of 0.5 CM carbon cloth catalyst supports. The prototype, as seen in FIG. 9, has a reactor (10) including a reactor body (100) having a reactor wall (110), a reactor lid (120), reactor lid clamps (130) and an exit port (140). In this approach, cloths were fixed inside a cylindrical reactor using retainer rings (see FIG. 9, element 220). However, after promising results with steel sheets in 7.5-cm tests, catalyst-coated stainless steel sheet reactor liners (with uncoated carbon cloth covering the exit) were also examined. As seen well in FIG. 9, the top of the reactor (10) was clamped shut using three 90° angle clamps (130) that compress a graphite gasket between the lid and a lip on the reactor. The reactor was housed in a vertically-mounted clamshell furnace, and an insulation cap (300) was placed over the top of the reactor and the clamps. Gas entered through the top-side of the cylinder, and exited, after passing through the cloth, out the bottom-center of the cylinder (Exit Port, element 140).

The goals of the alpha-prototype testing included:
1) Demonstrate that the target activity can be achieved at the 15-cm OD (~0.5 CM) scale;
2) Demonstrate activity targets for 100 hours of operation;
3) Test carbon removal procedures after 100 hours of operation;
4) Determine design changes for the next generation beta-prototype reactor; and
5) Perform tests to assist in failure mode analysis.

For each test, 900 to 1,200-cm² supports (carbon fiber cloths or stainless steel sheets/reactor liners) were coated with catalyst, then rolled up and activated in the 7.5-cm reactor. In some cases, the cloths were formed into a bag before activation. Unlike previous 7.5-cm testing, catalyst adhesion was more challenging at the larger scale due to a vertical orientation and the handling required to load the samples. Approximately 10% Sekisui BL-1 binder was used in the catalyst coatings unless otherwise specified. Tests were run with a gas composition of 40% CO, 40% $H_2$, 10% $CO_2$, 10% $N_2$, at the indicated flow rate. An overview of the tests completed is shown in FIG. 10 (Table 7).

The following important points from alpha-prototype testing are as follows, and details are discussed in the following paragraphs.
1) Steel sheets lining the reactor, with a carbon cloth disk covering the exit, held up better mechanically during long-term operation and through regeneration; no loss of catalyst activity was observed compared to carbon cloth in this configuration;
2) An Fe/Co hydroxide catalyst would enable resupply mass targets <1 kg/CM/yr to be achieved;
3) Activity above the target over 100 hours straight of operation was proven; and 4) The carbon product was soft and could be removed via vacuum.

In the initial test (FIG. 10; Table 7; Test 18-156) much of the catalyst fell off during processing, but the sample was tested for performance over 18 hours. The area-based activity was slightly lower than the target. In the next test (FIG. 10; Table 7; Test 18-159), the processing steps were improved to reduce catalyst losses, but area-based activity only improved by about 10%. In the next two tests (FIG. 10; Table 7; Tests 18-161 and 18-162), the catalyst loading was increased further, and area-based activity exceeded the target of 5 mg/cm²/hr, and carbon yield nearly reached 19% in the test. In all these tests, the growth rate per mass of catalyst was similar.

Next, long-term tests were run with carbon cloths. The first test (FIG. 10; Table 7; Test 18-163) examined a coated cloth over 93 hours of testing. The activity of the cloth was 4.3 mg/cm²/hr, just below the target of 5.0 mg/cm²/hr. The test was aborted before 100 hours due to an increase in pressure (up to 15.3 psia). The qualified limit for the reactor is ~2 psig, or 16.7 psia. Unfortunately, during removal of the bag containing carbon, the cloth ripped and a large portion of the carbon breached the bag.

After demonstration at the 7.5-cm (100-cm²) scale, a 900-cm² stainless steel sheet was also examined as the catalyst substrate in the alpha-prototype (FIG. 10; Table 7; Test 18-173). Over 79 hours the sheet did not match the activity obtained in the 7.5-cm reactor. The test was stopped before 100 hours due to a pressure increase caused by carbon growth in the exit line. Copper cladding was then added to the exit tube to prevent this. The next test (FIG. 10; Table 7; Test 18-179) examined a coated steel sheet over 68 hours of testing, at which point the inlet tube clogged with carbon and the test was aborted. In this test, carbon was partially removed every 18 hours and fresh catalyst was added via spray infiltration. The results show the aggregate values over 68 hours. The area-based activity of the cloth was 6.26 mg/cm$^2$/hr, exceeding the target of 5.0 mg/cm$^2$/hr. However, excessive catalyst loading was required due to the frequent re-infiltration, exceeding the 1 kg/yr/CM target by a factor of approximately 3. It should be noted that this catalyst mass is based on iron (III) nitrate.

In the next long-term 15-cm OD test, a stainless steel sheet was examined with a multi-layer base (steel mesh followed by carbon cloth, followed by alumina felt) that acts as a filter. The multi-layer base was added to keep as much carbon as possible inside of the reactor. The inlet tube was also replaced with a copper-lined inlet. In this test, carbon was not removed from the reactor until after completion. Additional catalyst was added every 20 hours in an attempt to maintain elevated activity by frequently introducing fresh catalyst. The catalyst loading over the entire run was consistent with the 1 kg/yr/CM target, assuming iron (III) nitrate basis. Over 100 hours the reactor operated without clogging; however, the performance did not match the activity targets. The final iron nitrate test (FIG. 10; Table 7; Test 18-187) examined a nitrate coated steel sheet over 104 hours of testing. In this test, fresh catalyst was added via spray infiltration (without carbon removal) at two intervals during the test. The results show the aggregate values over 104 hours. The area-based activity of the sheet was 5.10 mg/cm$^2$/hr, just exceeding the target of 5 mg/cm$^2$/hr. However, excessive catalyst loading was required due to the two re-infiltrations, exceeding the 1 kg/yr/CM target by a factor of approximately 2. Again, the catalyst is based on nitrates, which have 50% less metal by mass than hydroxides.

In the final alpha-prototype test, a stainless steel sheet coated with hydroxide-based catalyst with 30% cornstarch as binder was examined. The catalyst and cornstarch were mixed in water to form a viscous liquid, brush-coated on the steel sheet, then dried at 70° C. in an oven before loading in the reactor. The test ran for 100 hours with no reinfiltration of new catalyst. The catalyst loading was consistent with the target of less than 1 kg/yr/CM target. Over 100 hours the reactor achieved area-based activity of 6.52 mg/cm$^2$/hr, easily exceeding the target of 5 mg/cm$^2$/hr. FIG. 11 shows the product gas composition from the test (FIG. 10; Table 7, Test 18-199), and the estimated carbon yield based on an atomic balance. The carbon yield reported in Table 10 ("x" labelled data points) is based on the mass of carbon recovered after testing. Both measurements are in close agreement. The yield appears quite stable, and the target activity could probably have been achieved over longer than 100 hours. The carbon product was soft, and easily vacuumed from the reactor after testing.

Beta-Prototype Testing.

Based on the results from alpha-prototype testing, a beta-prototype CFR was built for testing. FIG. 12 shows a photograph of the beta-prototype reactor. Key changes included:
1) A longer feed line (including coil) was included to pre-heat gases. The line was entirely copper-clad. A thermocouple was added to the gas inlet for monitoring inlet temperature;
2) A ¼" Swagelok port with graphite ferrule was added to the lid to allow an agitator arm to be inserted into the reactor;
3) Addition of a 1.5" OD port with Swagelok cap for vacuum carbon removal;
4) A larger exit port with copper cladding to reduce risk of copper clogging; and
5) Bolted lid to reduce leaking.

For the beta-prototype, hydroxide catalyst and 30% cornstarch binder coated on stainless steel was used for most testing. For some tests, the stainless steel liner was initially spray-coated with aqueous catalyst precursor, then loaded and activated in the reactor before the test began. In other cases, the CFR was activated by in situ spraying of the walls with the catalyst precursor. Various carbon agitation approaches were examined, as will be discussed. Goals that were a focus of the beta-prototype testing included:
1) Shakedown testing to verify the reactor design functions as expected;
2) Increase to maturity of the technology by:
   a) Demonstrating >100 hours of catalyst operation before regeneration;
   b) Demonstrating vacuum carbon removal via the vacuum port;
   c) Demonstrating in situ catalyst spray injection regeneration;
   d) Perform tests to assist in failure mode analysis;
   e) Regenerate the same steel liner multiple times; and
   f) Demonstrate operation in humidified gas streams and updated compositions simulating integration with various system design options.

An overview of the results is given below in FIG. 13 (Table 8), and the details are discussed in the following paragraphs. Important results from the beta-prototype testing are as follow, and a detailed report of each test is given in the following paragraphs:
1) Activity targets were achieved over 100 hours with use of the optimized binder spray;
2) Pressure limits were reached after 130 hours (no agitation during test); 144 hours of testing was demonstrated with periodic agitation and pressure did not increase;
3) As high as 99% carbon removal through vacuum port was demonstrated with use of an agitator, and typically >97% of the carbon was removed;
4) in situ spray regeneration of the CFR was demonstrated;
5) Carbon cloth used on the reactor exit for filtering large particles demonstrated greater than 340 hours of durability;
6) Performance and regeneration was demonstrated with catalyst coating directly on the CFR wall (without using the stainless steel liner).

Initial Shakedown Testing.

An initial shakedown test (FIG. 13 (Table 8); Test 31-04) was run to confirm the reactor temperature profile, pressure drop, and initial performance match the expected values based on alpha-prototype results. The performance in this test was excellent, exceeding the targets and matching the previous results obtained in the alpha-prototype with brush-painted catalyst coating. Most of the carbon from this test was removed through the vacuum port; however, a significant portion of carbon fell and stuck to a stainless steel mesh and carbon cloth covering the bottom of the reactor (also covering the exit port). This carbon could not be removed through the vacuum port. Consequently, for the next test a "disk agitator" was added to the reactor.

The disk agitator consisted of a disk-shaped stainless steel mesh attached to a perpendicular steel rod that runs axially inside the reactor. The agitator allows carbon to be lifted towards the vacuum port. It remains to be determined if the disk agitator would be required in a microgravity environment. In the next test (FIG. 13 (Table 8); Test 31-015), the disk agitator was added to the reactor. Further, the hydroxide catalyst was milled and sprayed through a stainless steel nozzle. These changes resulted in decreased performance, so the test was aborted. Results from 7.5-cm testing discussed above indicate that the catalyst changes should not have decreased performance. Examination of the reactor after the test revealed that a significant amount of carbon formed or fell below the agitator through the mesh. For the third test (FIG. 13 (Table) 8; Test 31-024), the mesh agitator was replaced with a solid metal plate to prevent carbon/catalyst from falling below the exit port. While results improved, they did not quite match the targets, or the expected performance based on previous alpha-prototype tests. Post-test analysis revealed that catalyst/carbon adhesion was poor in this test and resulted in the initiation of the adhesion test previously discussed.

Table 8; Test 31-042; 100-hour Testing.

The coating process developed during the Adhesion Testing was implemented in the beta-prototype. A hydroxide slurry containing 30% cornstarch by weight was down-selected for coating. A stainless steel sheet was coated to a loading of 5 mg/cm$^2$. The sheet was loaded into the beta prototype reactor, purged with the standard CFR feed gas mixture and then reduced at 550° C. for 1 hour as usual. The reactor was then run for 130 hours at 475° C. GC injections were performed every 20 minutes. Carbon weight was determined at the end of the run. The run accumulated over 680 grams of solid carbon. The rate at which the carbon formed was well above the target rate. Furthermore, GC analysis over the 130 hour run, summarized in FIG. 6, indicates stable performance of the catalyst over the entire run. Accordingly, it appears that the improved coating and adhesion process developed was successful, resulting in the first beta-prototype run to reach the target of 100 hours at a growth rate above 5 mg$_{carbon}$/cm$^2$/hr. The extent of carbon formation was observed in the pressure change inside the reactor over the last 20 hours as can be seen in FIG. 15. The pressure rise is attributable to the build-up of carbon in the reactor and probably indicates the limit on the reactor runtime if intermittent agitation is not used.

Test 31-045; Spray Nozzle Regeneration.

In this test, a spray nozzle system was used for in-situ regeneration of the reactor. The steel liner from run 31-042 (FIG. 13 (Table 8); Test 31-042) was retained in the reactor after the test and then coated with catalyst using this atomizing nozzle approach for further testing. To do the infiltration, the reactor and steel liner, after run 31-042, was vacuumed free of carbon, not including any well-adhered carbon on the steel liner that could not be removed via vacuuming. A slurry containing hydroxide catalyst and 30% cornstarch was prepared. The slurry was then sprayed onto the steel liner while still inside of the reactor. Enough slurry was deposited so the steel liner would be coated with the target 5 mg/cm$^2$ of catalyst. In another change to the procedure for this run, mild agitation during the run was carried out every 24 hours to keep the carbon loose for subsequent carbon removal. The reactor was run as usual, with a 1 hour 550° C. reduction followed by 100 hours at 475° C. However, the agitator was intermittently moved every 20 hours. The reactor was run for 87 hours before shutting down due to the carbon monoxide supply running low. As shown in FIG. 13 (Table 8) and FIG. 16 the agitation was not detrimental to carbon formation.

After the run, a vacuum tube was inserted through the carbon removal port. The activity for the test, 6.86 mg/cm$^2$/hr was the highest obtained at this scale.

Test 31-057; Hot Spray Regeneration, Improved Agitator Design.

In the next test, two modifications were made to the reactor, seen well in FIGS. 17, and 22(a-b). As seen well in these figures, a reactor (10) may have a reactor wall (110) enclosing a reaction chamber (105), some or all of which may include a heated zone. There may be a fluid inlet port (150) as seen well in FIG. 22(b) and a fluid inlet pre-heat tube (155) as seen well in FIG. 17. Fluids may exit via exit port (140), seen well in FIGS. 17 and 22(b). An agitator assembly (400) may include an agitator shaft (410), at least one agitator arm (420), a spray nozzle (430), and an agitator coupling (440). A vacuum port (170), seen well in FIG. 17, allows access to remove carbon. An attrition zone (180), seen well in FIG. 22(b) may include blades or other devices to break up clumps of carbon. Filter media (210) may promote retention of catalyst, as seen well in FIGS. 17 and 22(b). At least a portion of the external surface of the reactor (10) may be covered with insulation (160) to promote heat retention.

The first modification was the addition of a rotating arm agitator (400). Previously, the disk agitator was moved up-and-down to dislodge carbon from the walls; however, this resulted in carbon being trapped below the disk (this trapped carbon is the primary carbon that cannot be removed through the vacuum port). With the new agitator design, the disk remains fixed to the bottom of the reactor while a rotating arm (420) removes carbon from the wall. The arm (420) is connected to a shaft (410) that extends out of the reactor, where it is sealed to a port. The shaft can be lifted or spun while the reactor is hot. Consequently, the arm (420) can move up-and-down and/or rotate, while the disk remains fixed. FIGS. 17 and 22 again illustrate a model of the design, although one skilled in the art will see this only an a non-limiting example. The second modification for this test was coating the liner while the reactor was heated to 300° C. This higher temperature regeneration would have advantages in turnaround time/efficiency. Unfortunately, at this temperature it appears the coating did not adhere well, as visual inspections prior to the test indicated. The low activity (4.17 mg/cm$^2$/hr) after the short run confirmed that catalyst adhesion was likely poor. With the new agitator, 88% of the carbon was removed through the vacuum port, and the remainder was removed after opening the lid for spray regeneration. Some additional carbon was observed under the disk, but this carbon was not removed nor was it accounted for. The trapped carbon was left in the reactor to determine if it would either (1) have any adverse effect on reactor performance, (2) will accumulate and clog gas flow, and/or (3) eventually damage the disk. It should be noted that this carbon can easily be removed by lifting the disk up or could be removed through an additional vacuum added to the bottom of the reactor. A more sophisticated reactor design (i.e. a lip on the bottom of the reactor that spans the gap between the disk and the walls) could also prevent carbon from falling below the disk.

Table 8; Test 31-061; Humidification Testing.

In the next test, the reactor liner was again spray-regenerated, this time while at ~100° C. wall temperature. Next, the CFR was run for over 100 hours with 10-mol % water added to the feed. Under these conditions the activity was below the target. For this test the water was injected through the inlet thermocouple port, thus no inlet temperature measurement could be obtained. It is possible that the poor activity can partially be blamed on a colder than typical inlet temperature, as the water could cool the gas ~150° C. After testing, the agitator arm was rotated and moved up-anddown to dislodge carbon from the walls. Next, the reactor was vacuumed out through the vacuum port. With this approach, 95% of the carbon formed was removed through the vacuum port. The remaining carbon was removed via vacuum from the walls after the lid was taken off for inspection and spray regeneration. Carbon that fell below the disk was left in the reactor again.

Table 8; Test 31-061; Reactor Demonstration.

The improved agitator was used in a 50-hour test with a dry feed so the carbon removal process and spray regeneration could be demonstrated. The reactor was not agitated, by spinning and lifting the agitator arm, until after the run was complete. With this approach, 99% of the carbon was removed through the vacuum port. The additional carbon was removed from the reactor walls after the CFR was opened, but before it was spray-regenerated. Carbon that fell below the disk was left in the reactor again.

Table 8; Test 31-075; Humidification Testing.

Humidification of the CFR feed was improved by the addition of a heater to the gas inlet (as opposed to the direct injection of water approach used in test 31-061 (FIG. 13 (Table 8)). The dry composition used was nominally 40% CO, 40% $H_2$, 10% $CO_2$, and 10% $N_2$ with 0.03 to 0.10 atm of water partial pressure. The heater was added to prevent cooling of the CFR, which may have occurred in test 31-61 (FIG. 13 (Table 8); Test 31-61). The performance improved with improved heating, but still fell just short of the target activity. It is believed that addition of water results in Water-Gas-Shift (WGS) conversion of CO to $CO_2$, and consequently, a higher $CO_2$:CO ratio could suppresses carbon formation equilibrium and kinetics.

Table 8; Test 31-081; Updated Conservative Composition for 144 Hours.

A long-term test was run using a composition based on integrated CFR-SOCE projections. The composition used was 41% CO, 18% $H_2$, 33% $CO_2$, 3% $H_2O$, and 5% $N_2$. This composition is also similar to the expected composition from a system that integrates with water electrolysis to hydrogen with a reverse water-gas-shift reactor as a means to generate carbon monoxide. As shown in FIG. 18, the test ran for 144 hours with steady carbon yield throughout the test. With the water and higher $CO_2$:CO ratio in the feed performance was lower than expected; however, the test did demonstrate vacuum carbon removal after a long run. With the periodic agitation of the reactor, the pressure drop did not increase during the test either. The methane yield with the new composition was much lower than previous tests (about 1.4%). This test demonstrated that the reactor can run for over 100 hours with periodic agitation, but more area or higher flows may be needed if the inlet feed has a high $CO_2$:CO ratio.

Table 8; Test 31-084; Conservative Composition, Higher Flow.

In the next test, the same gas composition as the previous test (FIG. 13 (Table 8); Test 31-081) was examined, but higher flow rates were used. If the CFR catalyst activity does not meet the target rate (5 mg/cm$^2$/hr) in a closed loop system with gas recycling, then the gas flows will increase until the carbon formation rate equilibrates with the systems incoming carbon dioxide flow. Using a higher flow rate, the carbon formation rate does indeed increase, as expected. At 50% increased flow rate the carbon formation rate was 4.77 mg/cm$^2$/hr, just below the target. Higher flows were not tested due to limitations with the mass flow controllers. Further, this was the first test in which the catalyst was coated directly on the CFR walls. The liner was initially used as a method to control and know precisely the catalyst mass in the reactor. The liner also is replaceable if carbon growth causes degradation of the steel; however, based on degradation testing (described in the section below) the liner does not lose mass during repeated cycle testing. The downside of the liner is that it can get caught on the agitator and disrupt carbon agitation/removal. Since the liner provides no benefit, it was decided to remove it from the prototype.

Table 8; Test 31-088; Ideal Composition.

In the final test with the beta-prototype, the integrated CFR-SOCE system stream composition was re-evaluated assuming more aggressive SOCE operation. The design subsection discusses the assumptions for that composition. By operating the SOCE under lower $CO_2$ concentration, the CFR inlet composition would be 51% CO, 16% $H_2$, 16% $CO_2$, 7% $H_2O$, and 10% $N_2$. With this inlet composition for the CFR, activity exceeded target performance. FIG. 19 shows the product gas composition from the testing. The water humidification was only 3% initially during the test (due to a thermocouple failure on the humidifier), at which point the carbon yield was estimated to be about 18%. When the water feed concentration increased to 7%, the yield dropped to about 13%. Overall, the average rate for the test was measured to be 6.67 mg/cm$^2$/hr based on the mass of carbon recovered from the CFR by vacuum.

System Design Concepts

CFR Concept of Operation

The concept of operation for an automated 4-CM flight system was created. For a 4-CM flight system, four CFR's could be packaged in parallel, as shown in the top-down view of FIG. 20. Four 1-CM CFR's could operate in parallel, each in its own insulated box. This would allow a CFR to be regenerated and/or serviced while the other reactors continue to run. Each is also equipped with its own pre-heater to return the CFR to temperature after cycling and maintain steady-state temperature. The estimated flow rate to each reactor would be ~4.4 slpm. The operating temperature would likely be 475° C. at steady-state, and pressure would be ~0.9 atm (sub-ambient operation). Sub-ambient pressure could be used to prevent outward leaks. The supporting valves, manifolds, and sensors required for CFR operation are shown schematically in the CFR-specific P&ID in FIG. 21. Gas from the electrolysis unit or other gas generating unit enters a manifold, from which it is equally distributed to the four CFRs. A preheater and temperature controllers ensures the correct feed temperature. The exit from the CFR passes through a filter and into another manifold before recycling back to the other system components. Valves allow for isolation of the CFR and could also be used to balance flow via pressure drop measurement. Valves also isolate the CFR from the vacuum system that is periodically used to remove carbon from all of the reactors.

Conceptual procedures, including valve switching, to operate the CFR during the various states are outlined below:

Start-up Operation (see FIG. 21):
1. V3 and V6 are opened to purge air from reactor.
2. V3 and V6 are closed, then V1 and V2 are opened to fill the reactor with non-oxidizing operating gas (Note: this step should occur after the SOCE is operating and producing a non-oxidizing atmosphere).
3. The pre-heater brings the CFR to 475° C. by pre-heating the inlet gas.

Steady State Operation:
1. Gas being fed from SOCE exhaust to CFR.
2. Every 24 hours the agitator spins once to prevent carbon blockage (no cooling required). 3. Reactor operates continuously for ~144 hours until pressure drop increases to 0.03 atm.

CFR Regeneration (after 144 Hours or ΔP=0.03 Atm at):
1. V1 and V2 are shut.
2. Reactor cools to <200° C. in ~3 hours.
3. V3 and V4 (FIG. 21) are opened.
4. Vacuum initiates, agitator rotates to loosen carbon.
5. Vacuum recirculates gas for 3 minutes through a filter bag to capture loose carbon.
6. V4 is closed, V6 is open (FIG. 21).
7. Gases are purged from reactor through V6 (FIG. 21).
8. Spray nozzle injects catalyst solution onto the reactor walls.
9. Steam is purged from reactor through V6, then V3 is closed (FIG. 21).
10. V1 is slowly opened to fill CFR with operating gas (FIG. 21).
11. V2 is opened, gas flows through the CFR (FIG. 21).
12. The preheater returns the CFR to 475° C. in 30 minutes by pre-heating the inlet gas.

Carbon Cleanout from Vacuum Operation (after ~4 kg of Carbon is Collected):
1. V6 is opened momentarily to purge out dangerous gases (FIG. 21), then shut.
2. Line and filter chamber is back-filled with air.
3. V5 (FIG. 21)(filter bag chamber lid) is opened.
4. Filter bag is tied shut and carbon is removed for transport to storage/use/disposal.
5. New filter bag is inserted (assuming filter bag cannot be re-used, depends on carbon disposal method).
6. V5 is shut (FIG. 21).
7. V6 is opened momentarily to purge out air (FIG. 21).
8. Line and chamber is back-filled with non-oxidizing SOCE exhaust gas by opening V4 momentarily (FIG. 21).

Automated CFR Design.

Based on test results with the 0.5 CM beta-prototype CFR, a third-generation (Gen3) CFR design capable of nearly complete automation was created. To minimize crew interaction, there are three main processes that needed to be automated: spray reinfiltration, carbon agitation, and carbon removal. The Gen3 reactor was designed to combine all of these actions into one simplified reactor. For spray reinifiltration, a spray nozzle sits in the middle of the reactor as seen in FIG. 22(b). The catalyst slurry is fed to the spray nozzle by the connected tubing, and then spins to coat the entire wall of the reactor. The spray nozzle will be spun by a small motor connected to the tubing extending outside of the hot zone of the system. The reactor will be heated during this process so that the sprayed catalyst dries once it comes into contact with the walls of the reactor. The spray nozzle will be made of a material that is resistant to carbon formation, such as copper or a ceramic, and will be flushed with water after spraying catalyst solution. The agitator system is also seen in FIG. 22(b), which extends below the spray nozzle, similar to the beta-prototype agitator. The two rods will be spun using the same motor that spins the spray nozzle. These rods break up carbon clumps near the bottom of the reactor to prevent the reactor from packing with carbon. This reduces the possibility of having to open the reactor in order to clear it of clogged carbon. As demonstrated in testing, the agitator would be spun every 24 hours to allow operation for at least 144 hours. The final part of the system to be automated is the carbon removal process. First, the large horizontal port seen in FIGS. 22a and 22b would be connected to a vacuum line. The vacuum is initiated to begin pulling the loose carbon up and out of the reactor. This approach was demonstrated in prototype testing; however, occasionally clogs or chunks of carbon have to be broken up in the vacuum line. To address potential clogging, while vacuuming is occurring, small blades, seen in the top of the lid in FIG. 22b, may be spun to break up any chunks of carbon as they were pulled out of the vacuum port. The blades may be spun by the same motor that spins both the spray nozzle and the agitating system. Thus the entire system is automated using a single spinning motor and the reactor can run without human intervention until maintenance is required.

Consumables

The largest replacement mass for the CFR is the catalyst and binder. Based on the concept of operation demonstrated in prototype testing, 790 g/CM/year of catalyst and binder will be consumed. With a density of 1.2 g/cc, this will store in 0.66 L/CM/year. Due to the powder nature of the catalyst, it can be stored in irregular shapes if a soft container is used.

ADDITIONAL EXAMPLES

The above disclosure provides examples of a CFR design with exceptionally low resupply mass and the ability to operate in an automated fashion. A number of variations to the design could be envisioned by on skilled in the art. Such variations could include, but are not limited to, the following:
1) Integration of the CFR with other various means of generating a reducing gas containing carbon, such as reverse water gas shift, Sabatier reactor, plasma reactor, pyrolysis reactor, or electrolysis;
2) Alternative methods for delivering catalyst into the reactor, such as dry catalyst particles, coated particles (i.e. beads, grains, or other high surface area shapes), coated reactor liners, or catalyst cartridges;
3) Alternative mechanical methods and designs for agitating the carbon so that it can be vacuumed and/or entrained in gas flow that carries it out of the reactor; and
4) Alternative catalyst compositions for formation of carbon, such as Fe, Co, Ni, Mn, Al, other transition metals, and mixtures thereof.
5) Alternative catalyst support materials that can withstand the operating conditions of the CFR 6) Alternative catalyst precursors such as metal nano-particles or materials that would decompose to catalytically active particles, such as various transition metal compounds including salts, organometallic compounds, oxides, hydroxides, metal alloys, carbides, and metal organic framework structures.

As used in this specification, a "transition metal compound" includes any compound that contains a transition metal, such as metal nitrates, metal acetates, metal oxides, metal hydroxides, elemental transition metals, metal carbides, metal hydrides, alloys, and mixtures thereof, while a transition metal is defined as one or more of the transitional metals as given in the Periodic Table and as well-known to one skilled in the art.

Further, the above disclosure provides examples of a CFR design for use in a spacecraft life-support system. The reactor design could also be used in a number of other applications, including:
1) Manufacturing of carbon nano-materials;
2) Oxygen recovery and/or sequestration of carbon in industrial and/or environmental applications;
3) Other life-support systems, including submarines.

What is claimed, then, includes a chemical composition bearing a mixture suitable for use in forming solid carbon from carbon-containing fluid in a non-oxidizing atmosphere.

The composition further may include an organic binder; and a solid catalyst precursor component that includes a transition metal compound. In some embodiments, the transition metal compound may be selected from the group of compounds consisting of hydroxides, oxides, carbides, alloys, hydrides and mixtures thereof. In other embodiments, the transition metal component of the transition metal compound may be selected from the group of transition metals consisting of iron, cobalt, nickel, manganese, and mixtures thereof.

In other embodiments, the binder may be water soluble, and in others, the transition metal compound may equal to or more than 25-wt % of a solids mass of the composition, while in yet others, the transition metal compound may equal to or more than 10-wt % of a solids mass of the composition. The composition is an aqueous suspension.

Also claimed is a chemical reactor (10), seen well in FIGS. 17 and 22(a-b), including a reactor (10) suitable for use for forming carbon from a carbon-containing fluid in a non-oxidizing atmosphere. Such a reactor (10) may further include a fluid inlet port (150) in fluid communication with a reaction chamber (105) having a heated zone. The reaction chamber (105) may have a reusable catalyst-coated substrate within the heated zone in the reaction chamber (105) in fluid communication with an exit port (140). Carbon may be extracted from the carbon-containing fluid onto the substrate and the reaction chamber (105) may have a means for periodically loosening carbon from the substrate.

In further embodiments, the reactor (10) may include a valve system suitable for use in automated carbon removal from the reactor (10), a vacuum port (170) in fluid communication with the reaction chamber (105), and/or a spray nozzle (430) suitable for use in delivery of a catalyst coating into the reaction chamber (105). In yet other embodiments, wherein the reaction chamber (105) further comprises a filter media (210) suitable for use in retaining catalyst in the heated zone of the reaction chamber (105). In yet other embodiments, the reactor (10) further comprises a mechanical means for periodically loosening carbon from the filter media (210). In others, the reusable substrate further comprises a portion of a reaction chamber wall (110).

Together, the composition and the reactor (10) may be used in a method for producing carbon that includes the steps of; a) coating a substrate with a mixture comprising binder and a predetermined mass of catalyst precursor particles selected from the group of particles consisting of forms of iron, cobalt, nickel, manganese and mixtures thereof; b) heating the catalyst coated precursor; c) exposing the catalyst-coated precursor to a non-oxidizing fluid stream containing carbon, thereby; d) forming a mass of carbon equal to or greater than ten (10) times the mass of catalyst precursor; and e) separating the carbon from the substrate. Steps (b) through (e) may be repeated in a cyclic function.

In some embodiments, the substrate may be coated by spraying with at least one catalyst precursor. The catalyst precursor particles may include metal hydroxide particles, and the mixture may be an aqueous suspension In other embodiments, the catalyst precursor particles further include transition metal compounds such that the transition metal compounds m equal to or greater than 25-wt % of a solid mass of the catalyst and binder; while in others, the catalyst precursor particles further comprise transition metal compounds such that the transition metal compounds may be equal to or greater than 10-wt % of a solid mass of the catalyst and binder.

In other embodiments of the method, the step of heating the catalyst-coated precursor may include a step of heating the catalyst-coated precursor to between about 350° C. and 650° C. In yet other embodiments, the step of forming a mass of carbon equal to or greater than ten (10) times the mass of catalyst precursor further comprises a step of forming a mass of carbon equal to or greater than one hundred (100) times the mass of the catalyst precursor.

In certain embodiment's, the step of separating the carbon from the substrate may include a step of using gas flow to separate the carbon from the substrate.

Numerous alterations, modifications, and variations of the preferred embodiments disclosed herein will be apparent to those skilled in the art and they are all anticipated and contemplated to be within the spirit and scope of the disclosed specification. For example, although specific embodiments have been described in detail, those with skill in the art will understand that the preceding embodiments and variations can be modified to incorporate various types of substitute and or additional or alternative materials, relative arrangement of elements, order of steps and additional steps, and dimensional configurations. Accordingly, even though only few variations of the method and products are described herein, it is to be understood that the practice of such additional modifications and variations and the equivalents thereof, are within the spirit and scope of the method and products as defined in the following claims. The corresponding structures, materials, acts, and equivalents of all means or step plus function elements in the claims below are intended to include any structure, material, or acts for performing the functions in combination with other claimed elements as specifically claimed.

We claim:

1. A chemical reactor (10) comprising:
 a carbon-containing fluid;
 a fluid inlet port (150) in fluid communication with a reaction chamber (105) having a heated zone;
 a reaction chamber (105) having a fixed catalyst-coated surface wherein the catalyst is attached, by a binder present on the catalyst surface, directly to a fixed substrate, secured inside the reactor (10) comprising a reusable catalyst-coated substrate further comprising at least a majority of a reaction chamber wall within the heated zone in the reaction chamber (105) in fluid communication with an exit port (140); and
 wherein carbon is extracted from the carbon-containing fluid onto the substrate where a majority of the carbon is adherent irrespective of gravitational direction and the reaction chamber (105) further comprises a means for periodically loosening carbon from the substrate without exposing the substrate to ambient atmosphere.

2. The chemical reactor of claim 1 wherein the reactor (10) further comprises a valve system for automated carbon removal from the reactor (10).

3. The chemical reactor of claim 1 wherein the reaction chamber (105) is in fluid communication with a vacuum port (170).

4. The chemical reactor of claim 1 wherein the reactor (10) further comprises a spray nozzle (430) for delivering a catalyst coating into the reaction chamber (105).

5. The chemical reactor of claim 1 wherein the reaction chamber (105) further comprises a filter media (210) retaining catalyst in the heated zone of the reaction chamber (105).

6. The chemical reactor of claim 1 wherein the means for periodically loosening carbon from the substrate without exposing the substrate to ambient atmosphere further comprises a mechanical means for periodically loosening carbon from a filter media (210) retaining catalyst in the heated zone of the reaction chamber (105).

7. The chemical reactor of claim 1, wherein a coating on the catalyst-coated substrate comprises a binder and a transition metal precursor.

8. The chemical reactor of claim 1, wherein a coating on the catalyst-coated substrate comprises a binder and a transition metal precursor, and wherein the transition metal precursor is selected from the group of compounds consisting of hydroxides, oxides, carbides, alloys, hydrides and mixtures thereof.

9. The chemical reactor of claim 1, wherein the catalyst-coated substrate further comprises a majority of a surface area of the reaction chamber walls.

10. The chemical reactor of claim 1, wherein the catalyst-coated substrate further comprises an organic binder.

11. The chemical reactor of claim 1, wherein the majority of carbon is adherent irrespective of gravitational direction for at least 18 hours.

12. The chemical reactor of claim 1, wherein the reactor (10) is a reactor selected from the group of reactors consisting of catalyst-coated carbon cloth, woven carbon fiber cloth bags with a fixed collar, woven carbon cloth bags strapped to the outside of an inlet tube, flat catalyst coated sheets, catalyst coated reactor liners, and a catalyst coated reactor wall.

13. A chemical reactor (10) comprising:
a carbon-containing fluid;
a fluid inlet port (150) in fluid communication with a reaction chamber (105) having a heated zone;
the reaction chamber (105) comprising a reusable catalyst-coated substrate wherein the catalyst is adhered, by a binder present on the catalyst surface, directly to the substrate and irrespective of gravitational direction within the heated zone in the reaction chamber (105) in fluid communication with an exit port (140); and
wherein carbon is extracted from the carbon-containing fluid onto the substrate where a majority of the carbon is adherent irrespective of gravitational direction and the reaction chamber (105) further comprises a means for periodically loosening carbon from the substrate without opening the reaction chamber (105) to an ambient atmosphere.

14. The chemical reactor of claim 13 wherein the reactor (10) further comprises a spray nozzle (430) delivering a catalyst coating into the reaction chamber (105).

15. The chemical reactor of claim 13, wherein a coating on the catalyst-coated substrate further comprises a binder and a transition metal precursor.

16. The chemical reactor of claim 13, wherein the catalyst-coated substrate comprises a binder and a transition metal precursor, and wherein the transition metal precursor is selected from the group of compounds consisting of hydroxides, oxides, carbides, alloys, hydrides and mixtures thereof.

17. The chemical reactor of claim 13 wherein the reaction chamber (105) further comprises a filter media (210) retaining catalyst in the heated zone of the reaction chamber (105).

18. The chemical reactor of claim 13 wherein the means for periodically loosening carbon from the substrate without exposing the substrate to ambient atmosphere further comprises a mechanical means for periodically loosening carbon from a filter media (210) retaining catalyst in the heated zone of the reaction chamber (105).

19. A chemical reactor (10) comprising:
a carbon-containing fluid;
a fluid inlet port (150) in fluid communication with a reaction chamber (105) having a heated zone;
the reaction chamber (105) comprising an organic binder directly adhering a catalyst and a fixed catalyst-coated substrate, secured within the heated zone in the reaction chamber (105), in fluid communication with an exit port (140); and
wherein carbon is extracted from the carbon-containing fluid onto the substrate wherein a majority of the carbon is adherent irrespective of gravitational direction and the reaction chamber (105) further comprises a means for periodically loosening carbon from the substrate.

20. The chemical reactor of claim 19, wherein the loosened carbon is periodically removable from the reaction chamber (105) without opening the reaction chamber (105) to an ambient atmosphere.

21. The chemical reactor of claim 19, wherein a coating on the catalyst-coated substrate comprises a binder and a transition metal precursor.

22. The chemical reactor of claim 19, wherein a coating on the catalyst-coated substrate comprises a binder and a transition metal precursor, and wherein the transition metal precursor is selected from the group of compounds consisting of hydroxides, oxides, carbides, alloys, hydrides and mixtures thereof.

23. The chemical reactor of claim 19 wherein the reaction chamber (105) further comprises a filter media (210) retaining catalyst in the heated zone of the reaction chamber (105).

24. The chemical reactor of claim 19 wherein the means for periodically loosening carbon from the substrate without exposing the substrate to ambient atmosphere further comprises a mechanical means for periodically loosening carbon from a filter media (210) retaining catalyst in the heated zone of the reaction chamber (105).

* * * * *